United States Patent [19]

Tai et al.

[11] Patent Number: 5,648,449

[45] Date of Patent: Jul. 15, 1997

[54] COPOLYESTERS, MOLDED ARTICLES FROM THE SAME AND AROMATIC TRIOLS USED FOR PRODUCING THE SAME

[75] Inventors: Shinji Tai; Tetsuya Hara; Akira Kageyu; Tsugunori Kashimura, all of Kurashiki, Japan

[73] Assignee: Kuraray Co., Ltd., Kurashiki, Japan

[21] Appl. No.: 594,948

[22] Filed: Jan. 31, 1996

[30] Foreign Application Priority Data

| Jan. 31, 1995 | [JP] | Japan | 7-013523 |
| Jan. 31, 1995 | [JP] | Japan | 7-032803 |
| Feb. 1, 1995 | [JP] | Japan | 7-034710 |

[51] Int. Cl.$^6$ .............................. C08G 63/18; B32B 1/08; C07C 43/11; B29C 47/00; B29C 17/07
[52] U.S. Cl. .................. 528/193; 528/176; 528/190; 528/195; 528/212; 528/219; 528/272; 528/294; 528/295; 528/298; 528/300; 528/308; 528/308.6; 528/503; 264/540; 428/35.7; 568/28; 568/33; 568/34; 568/593; 568/607
[58] Field of Search ................... 528/176, 190, 528/193, 195, 212, 219, 272, 294, 295, 298, 300, 308, 308.6, 503; 264/540; 428/35.7; 568/28, 33, 34, 593, 607

[56] References Cited

U.S. PATENT DOCUMENTS

| 4,161,579 | 7/1979 | Edelman et al. | 525/444 |
| 4,182,841 | 1/1980 | Hauenstein | 525/437 |
| 4,188,357 | 2/1980 | Go | 264/540 |
| 4,219,527 | 8/1980 | Edelman | 264/540 |
| 4,234,708 | 11/1980 | Edelman | 525/444 |
| 4,547,563 | 10/1985 | Cholod | 528/173 |

FOREIGN PATENT DOCUMENTS

| 0 119 731 | 9/1984 | European Pat. Off. . |
| 0 415 728 | 3/1991 | European Pat. Off. . |
| 2 010 295 | 6/1979 | United Kingdom . |

*Primary Examiner*—Samuel A. Acquah
*Attorney, Agent, or Firm*—Oblon, Spivak, McClelland, Maier & Neustadt, P.C.

[57] ABSTRACT

A copolyester consisting essentially of ethylene terephthalate units and further comprising 0.01 to 1 mole % based on the sum of the moles of total diol units and the moles of triol units of a triol unit represented by the following formula (I) and/or a triol unit represented by the following formula (II).

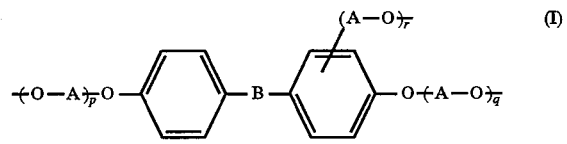

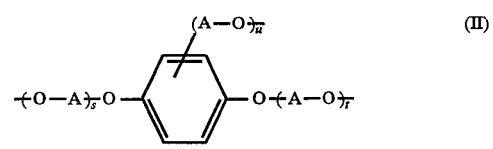

wherein A is a group represented by formula —$CH_2CH_2$— or formula —$CH(CH_3)CH_2$—, B is a divalent hydrocarbon group, —CO—, —$SO_2$—, —O— or a direct bond (–), and p, q, r, s, t and u are each an integer of 1 to 8. A process for producing the same and molded articles (in particular extrusion blow molded articles) therefrom. The copolyesters of the present invention are applicable to melt moldings accompanying melt extrusion, in particular extrusion blow molding, where parisons therefrom have good draw-down tendency and blow moldability. The copolyesters can give, without causing troubles on molding, molded articles, in particular extrusion blow molded articles, having excellent transparency, heat resistance, moisture resistance and like properties. Aromatic triols usable for producing the above copolyesters are also provided.

20 Claims, No Drawings

COPOLYESTERS, MOLDED ARTICLES FROM THE SAME AND AROMATIC TRIOLS USED FOR PRODUCING THE SAME

BACKGROUND OF THE INVENTION

1. Field of the Invention

The present invention relates to copolyesters, processes for producing the same and aromatic triols used for the production of the same; and, further, to a process for producing molded articles therefrom and molded articles obtained from said process. The copolyesters of the present invention have a high melt viscosity and have the non-Newtonian characteristics of exhibiting low viscosity at high shear rates and high viscosity at low shear rates, and are hence applicable to various molding processes, in particular to extrusion blow molding to produce hollow molded articles.

2. Description of the Prior Art

Resins of polyesters such as polyethylene terephthalate are excellent in various features such as transparency, mechanical properties, gas barrier properties and flavor barrier properties and, cause little worry with respect to residual monomers and toxic additives, in hygiene and safety, when molded into shaped articles. The resins have therefore become widely used in recent years, while replacing polyvinyl chloride resin, for hollow containers to be filled with juices, soft drinks, relishes, oil, cosmetics, cleansers and similar items.

Two representative processes for producing hollow shaped articles such as plastic containers are extrusion blow molding which comprises extruding a melt plasticized resin through a die-orifice into a cylindrical parison and, while holding the parison as it is still softened, blowing a fluid such as air into the parison; and injection blow molding which comprises injecting a melted resin into a die to mold a closed parison (preforms) once and, after inserting it into a blow die, blowing a fluid such as air into the preforms.

Of the above processes, the former, i.e., extrusion blow molding, is simpler than the latter, i.e., injection blow molding, and requires no complex techniques to prepare dies and for molding, and hence requires only the cost of equipment and die preparation. Extrusion blow molding is therefore suitable for multiple-product-small-quantity production and, further, has the advantage of being capable of producing thin, thick or large articles and complex-shaped articles having a knob or like irregular fittings.

Various attempts have therefore been made to conduct extrusion blow molding with general-purpose polyesters, such as polyethylene terephthalate and polybutylene terephthalate. However, general-purpose polyesters generally have low melt viscosity, so that, when they are extrusion blow molded, the parisons extruded markedly sag (drawdown) and become difficult to shape. In addition, crystallization tends to occur on blowing after extrusion, thereby reducing the transparency or shapability. These disadvantages of conventional polyesters as caused by their low melt viscosity and ready crystallizability are more marked when they are extrusion blow molded into long parisons having a length of, generally, 20 cm or more, which is required for producing large-size hollow molded shaped articles. As a result, it becomes very difficult to obtain shaped articles, in particular large ones, having a uniform shape and size and, at the same time, good transparency from conventional polyesters by extrusion blow molding.

For the above reason, in conducting extrusion blow molding, there have been used polyvinyl chloride and polyolefin resins, which have high melt viscosity and cause the extruded parisons in a melted condition to sag only to a small extent. However, extrusion blow molded articles from polyvinyl chloride resin have some hygiene or safety problems with respect to elution of toxic additives such as plasticizers and metal-containing stabilizers and, further, in that incineration of waste of the molded articles generates toxic gases. Their use has therefore been decreasing in Europe and other areas. Extrusion blow molding with polyolefins such as polyethylene results in shaped articles becoming white turbid due to crystals, so that the articles tend to have poor transparency and appearance.

In view of the above, several proposals with respect to polyester resins applicable to extrusion blow molding have therefore been made, including:

① U.S. Pat. No. 4,161,579, 4,219,527, 4,234,708 and 4,182,841 and Japanese Patent Application Laid-open No. 92730/1980 disclose a process for producing polyester applicable to extrusion blow molding, which comprises subjecting a dicarboxylic acid component such as terephthalic acid or ester-forming derivatives thereof and a diol component such as ethylene glycol to esterification or transesterification to obtain a low-polymerization-degree compound, reacting with the compound a conventional crosslinking agent such as trimethylolpropane, pentaerythritol or trimellitic acid to prepare a prepolymer and subjecting the prepolymer to solid phase polymerization;

② A process which comprises, on producing polyethylene terephthalate, polybutylene terephthalate or the like, copolymerizing isophthalic acid or cyclohexane dimethanol is known; and ③ EP 0532943A1 discloses a process for producing modified polyesters, which comprises adding, on producing polyethylene terephthalate, polybutylene terephthalate or the like, an ethylene oxide adduct of bisphenol A.

However, polyesters obtained by the above process ① give extrusion blow molded articles having no transparency with marked whitening due to formation of spherulites resulting from increased rate of crystallization. Further, in some cases, gels generate which are caused by crosslinking and cause the resulting shaped articles to contain agglomerates, thereby marring their appearance.

The present inventors have, based on the above known art ②, produced polyethylene terephthalate-based copolymers with the melting point decreased, by copolymerizing isophthalic acid or cyclohexane dimethanol and attempted to carry out extrusion blow molding with these copolyesters while setting the melt extrusion temperature at a lower temperature than before. However, because of the melt viscosity being not sufficiently high at the extrusion temperature, the parisons extruded upon extrusion molding sagged markedly and were difficult to shape, so that the extrusion blow molding operation could not be run smoothly. Furthermore, with the copolyesters copolymerized with isophthalic acid or cyclohexane dimethanol obtained by the prior art ②, solid phase polymerization could not be conducted or, if ever conducted, proceeded too slowly to achieve a sufficiently high degree of polymerization. As a result, shaped articles prepared from these copolyesters had a large dispersion of thickness and poor transparency.

The present inventors also conducted a follow-up experiment with the known art copolyester of the above ③, copolymerized with an ethylene oxide adduct of bisphenol A, to find that its extrusion blow moldability was not sufficient.

The present inventors have also attempted, separate from the known art of above ① through ③, to produce by solid phase polymerization a polyethylene terephthalate having a high degree of polymerization. However, it was found that the rate of the solid phase polymerization was very low, so that it was impossible to produce, in a short period of time and efficiently, a polyethylene terephthalate having a sufficiently high degree of polymerization and melt viscosity suitable for extrusion blow molding and like processes. This method is hence not applicable in practice from the viewpoint of productivity.

Accordingly, an object of the present invention is to provide a polyester having excellent melt moldability with high melt viscosity, in particular excellent extrusion blow moldability, which can yield, when extrusion blow molded, an extruded parison causing no severe drawdown, and shaped articles having desired shape and size, at high precision and smoothly.

Another object of the present invention is to provide a polyester which can give smoothly, on melt molding, in particular on extrusion blow molding, shaped articles having excellent transparency and heat resistance.

A further object of the present invention is to provide a process for producing, in a short period time and at high productivity, polyesters having the above excellent features.

A still further object of the present invention is to provide a process for producing shaped articles from the above polyesters having excellent features by melt molding, in particular extrusion blow molding and, also to provide shaped articles obtained therefrom.

A still further object of the present invention is to provide an aromatic triol which does not form gel-like agglomerates and has a large effect on increasing the rate of polymerization, and is hence useful as a crosslinking agent and a resin-modifying agent.

SUMMARY OF THE INVENTION

As a result of an intensive study made by the present inventors to achieve the above objects, it has been found that, on producing a polyester from a dicarboxylic acid component consisting essentially of terephthalic acid or ester-forming derivatives thereof and a diol component consisting essentially of ethylene glycol, ① use of a specific amount of a specific triol component having a benzene ring leads to production of a copolyester that is excellent in the above melt moldability and, at the same time, in transparency and heat resistance, and ② use of a specific amount of the above specific triol in combination with a specific amount of a specific diol having a benzene ring can yield a copolyester having excellent mechanical properties such as impact resistance, as well as the above excellent melt moldability, transparency and heat resistance. It has also been found that copolyesters can be obtained, in a short period time and at good productivity, by effecting esterification or transesterification with the above dicarboxylic acid component, diol components and triol component, melt condensing the obtained reaction product to form a polyester prepolymer and subjecting the prepolymer to solid phase polymerization.

The present inventors have made a further study of the properties and moldability of the above copolyesters to find the following facts. That is, the copolyesters exhibit non-Newtonian properties, having a low viscosity at high shear rates and a high viscosity at low shear rates, and are hence suitable for various melt molding processes, in particular extrusion blow molding. The copolyesters, when extrusion blow molded, give parisons causing no severe drawdown and thus have good blow moldability. With the copolyesters, it is possible to produce smoothly molded articles having the desired shape and size at high precision and high productivity, the articles being excellent in transparency, mechanical properties, heat resistance and like features. Based on these findings, the present inventors have completed the invention.

The present invention provides a copolyester (hereinafter referred to as "copolyester (A)") comprising:

(i) diol units consisting essentially of ethylene glycol units and dicarboxylic acid units consisting essentially of terephthalic acid units, said copolyester further comprising:

(ii) at least one group of triol units selected from the group consisting of:
(a) triol units (I) each represented by the following formula (I)

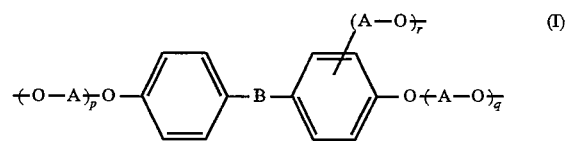

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and p, q and r are each, independently, an integer of 1 to 8; and (b) triol units (II) each represented by the following formula (II)

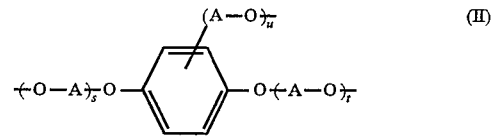

wherein A is a group represented by formula —CH$_2$CH$_2$— or formula —CH(CH$_3$) CH$_2$—, and s, t and u are each, independently, an integer of 1 to 8, in an amount of about 0.01 to 1 mole % based on the sum of the moles of total diol and said triol units.

The present invention also provides a copolyester (hereinafter referred to as "copolyester (B)") comprising:

(i) diol units consisting essentially of ethylene glycol units and dicarboxylic acid units consisting essentially of terephthalic acid units, said copolyester further comprising:

(ii) at least one group of diol units selected from the group consisting of:
(a) diol units (III) each represented by the following formula (III)

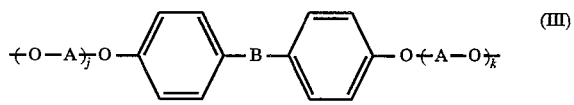

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and j and k are each, independently, an integer of 1 to 8; and (b) diol units (IV) each represented by the following formula (IV)

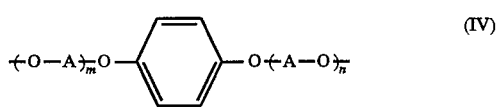

(IV)

wherein A is a group represented by formula —CH$_2$CH$_2$— or formula —CH(CH$_3$)CH$_2$— and m and n are each, independently, an integer of 1 to 8, and (iii) at least one group of triol units selected from the group consisting of:

(a) triol units (I) each represented by the following formula (I)

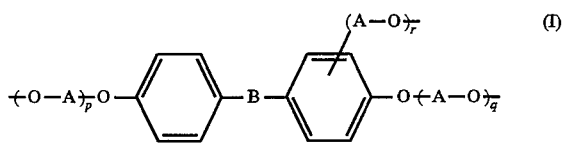

(I)

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and p, q and r are each, independently, an integer of 1 to 8; and (b) triol units (II) each represented by the following formula (II)

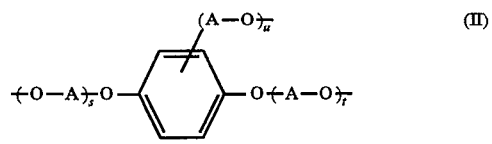

(II)

wherein A is a group represented by formula —CH$_2$CH$_2$— or formula —CH(CH$_3$)CH$_2$—, and s, t and u are each, independently, an integer of 1 to 8, and (iv) said at least one group of diol units selected from the group consisting of diol units (III) and diol units (IV) being contained in an amount of about 1 to 15 mole % based on the sum of the moles of total diol and said triol units, and (v) said at least one group of triol units selected from the group consisting of triol units (I) and triol units (II) being contained in an amount of about 0.01 to 1 mole % based on the sum of the moles of total diol and said triol units.

The present invention further relates to molded articles, in particular extrusion blow molded articles and, also, to a process for producing molded articles from the above copolyesters by conducting extrusion blow moldings The present invention still further provides a process for producing the above copolyester (A), which comprises subjecting to esterification or transesterification starting materials comprising:

(1) a dicarboxylic acid component consisting essentially of terephthalic acid or ester-forming derivatives thereof;

(2) a diol component consisting essentially of ethylene glycol; and (3) a triol component containing at least one triol selected from the group consisting of:

(a) a triol represented by the following formula (V)

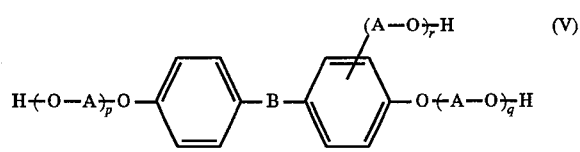

(V)

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and p, q and r are each, independently, an integer of 1 to 8; and (b) a triol represented by the following formula (VI)

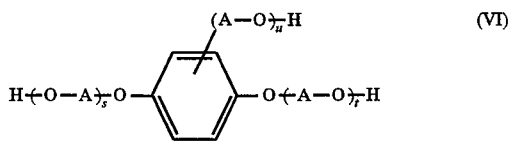

(VI)

wherein A is a group represented by formula —CH$_2$CH$_2$— or formula —CH(CH$_3$)CH$_2$—, and s, t and u are each, independently, an integer of 1 to 8, in an amount of about 0.01 to 1 mole % based on the sum of the moles of total diol and said triol components;

melt polycondensing the obtained reaction product to form a polyester prepolymer; and subjecting the polyester prepolymer to solid phase polymerization.

The present invention yet further provides a process for producing the above copolyester (B), which comprises subjecting to esterification or transesterification starting materials comprising:

(1) a dicarboxylic acid component consisting essentially of terephthalic acid or ester-forming derivatives thereof;

(2) a diol component consisting essentially of ethylene glycol and containing at least one diol selected from the group consisting of:

(a) a diol represented by the following formula (VII)

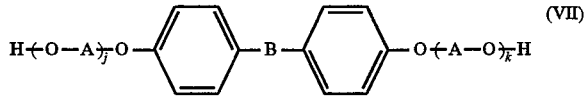

(VII)

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and j and k are each, independently, an integer of 1 to 8; and (b) a diol represented by the following formula (VIII)

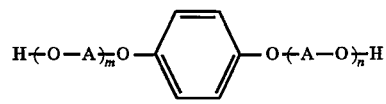

(VIII)

wherein A is a group represented by formula —CH$_2$CH$_2$— or formula —CH(CH$_3$)CH$_2$—, and m and n are each, independently, an integer of 1 to 8, in an amount of about 1 to 15 mole % based on the sum of the moles of total diol and said triol components; and (3) a triol component containing at least one triol selected from the group consisting of a triol represented by the above formula (V) and a triol represented by the above formula (VI), in an amount of about 0.01 to 1 mole % based on the sum of the moles of total diol and said triol components;

melt polycondensing the obtained reaction product to form a polyester prepolymer; and subjecting the polyester prepolymer to solid phase polymerization.

The present invention yet further provides an aromatic triol represented by the following formula (V)

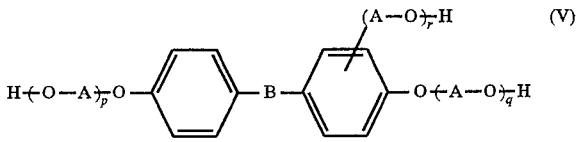

wherein A is a group represented by formula —$CH_2CH_2$— or formula —$CH(CH_3)CH_2$—, B is a divalent hydrocarbon group, a carbonyl group, a sulfonyl group, an oxygen atom or a direct bond (–), and p, q and r are each, independently, an integer of 1 to 8;

and an aromatic triol component represented by the following formula (VI)

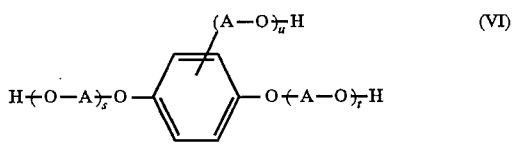

wherein A is a group represented by formula —$CH_2CH_2$— or formula —$CH(CH_3)CH_2$— and s, t and u are each, independently, an integer of 1 to 8.

DETAILED DESCRIPTION OF THE PREFERRED EMBODIMENTS

The copolyesters (A) and (B) of the present invention principally comprise diol units consisting essentially of ethylene glycol units and dicarboxylic acid units consisting essentially of terephthalic acid units, and it is necessary that these copolyesters further comprise, together with the above diol units and dicarboxylic units, at least one group of units selected from the group consisting of triol units (I) represented by the above formula (I) and triol units (II) represented by the above formula (II).

The copolyesters of the present invention may comprise as triol units either one or both of the triol units (I) and triol units (II).

In the triol units (I) and triol units (II), the group A is a group (ethylene group) represented by formula —$CH_2CH_2$— or a group (1,2-propylene group) represented by formula —$CH(CH_3)CH_2$—. With the copolyesters of the present invention and with the triol units (I) and/or triol units (II) contained therein, all of the group A may be an ethylene group, all of the group A may be an 1,2-propylene group, or part of the group may be an ethylene group with the rest being a 1,2-propylene group. Among these embodiments, it is desirable, that the group A in the triol units (I) and/or triol units (II) in the copolyesters be an ethylene group in view of easiness of production of the copolyesters and production cost.

The group B in the triol units (I) is a divalent hydrocarbon group, a carbonyl group, a sulfonyl group, an oxygen atom or a direct bond (–). Where the group B is a divalent hydrocarbon group, the group is desirably an alkylene group or alkylidene group having 1 to 8 carbon atoms or a divalent aromatic group. Examples of desirable divalent hydrocarbon groups are methylene group, ethylene group, ethylidene group, 1,2-propylene group, propylidene group, trimethylene group, isopropylidene group, butylidene group, ethylethylene group, tetramethylene group, 1-methylpropylidene group, 1,2—dimethylethylene group, pentylidene group, 1-methylbutylidene group, pentamethylene group, 1-ethyl-2-methylethylene group, 1,3-dimethyltrimethylene group, 1-ethylpropylidene group, trimethylethylene group, isopropylmethylene group, 1-methylbutylidene group, 2,2-dimethylpropylidene group, hexamethylene group, 1-ethylbutylidene group, 1,2-diethylethylene group, 1,3-dimethylbutylidene group, ethyltrimethylethylene group, heptamethylene group, octamethylene group, 1,1-cyclopentylidene group, 1,1-cyclohexylidene group, 1,1-cycloheptylidene group, 1,1-cyclooctylidene group, benzylidene group and 1-phenylethylidene group.

With the copolyesters of the present invention, the group B contained in the triol units (I) present in the copolyesters may be the same or different. Among the above, the group B in the triol units (I) of the copolyesters of the present invention is preferably an isopropylidene group, sulfonyl group and/or 1,1-cyclohexylidene group, which leads to good thermal stability of the copolyesters on melting.

With the copolyesters of the present invention, p, q, r, s, t and u in the triol units (I) and triol units (II) are each independently an integer of 1 to 8. The p, q, r, s, t and u may therefore be the same or different. It is desirable that, in particular, p, q, r, s, t and u be each independently an integer of 1 or 2, which leads to good thermal stability of the copolyesters on melting.

Further with the copolyesters of the present invention, it is particularly preferred in view of production cost and ease of production and melt stability of the copolyesters, that the triol units (I) and (II) be represented by the following formulas (IX) and (X), respectively:

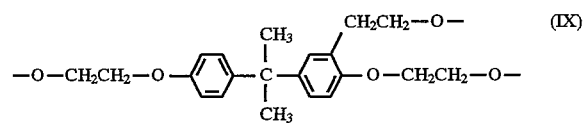

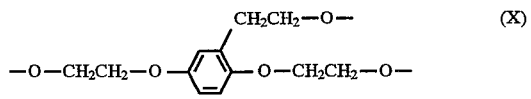

It is necessary that the copolyesters of the present invention comprise at least one group of units selected from the group consisting of triol units (I) and triol units (II) in an amount (when containing both, the total amount thereof) of 0.01 to 1 mole % based on the sum of the moles of total diol and said triol units (i.e. at least one group of triol units selected from the group consisting of triol units (I) and triol units (II)) constituting the polyesters. In other word, the copolyesters should contain 0.01 to 1 mole of triol units (I) and/or triol units (II) based on 100 moles of the sum of total diol units and these triol units.

If the triol units (I) and/or triol units (II) are contained in an amount of less than 0.01 mole %, the moldability on melt molding, such as extrusion blow molding, is poor, so that, in particular on extrusion blow molding, the extruded parison sags severely and close and does not yield hollow articles having good shape. In addition, with the amount being less than 0.01 mole %, the rate of solid phase polymerization on producing copolyesters decreases, thereby decreasing the productivity thereof.

On the other hand, if the content of the triol units (I) and/or triol units (II) exceeds 1 mole %, the resulting copolyester will have too large a crosslinked structure, and cause gels to generate caused by the crosslinked structure, so that, on producing molded articles, problems occur such as generation of agglomerates and whitening, which impair their appearance. In order to prevent generation of gels, one may attempt to decrease the degree of polymerization of the copolyesters, which however decreases the level of entanglement between molecules and causes the resulting molded articles to have insufficient mechanical strength. Besides, if the content of the triol units (I) and/or triol units (II) exceeds 1 mole %, the rate of crystallization becomes, on production of molded articles, too high, so that spherulites generate and the molded articles are whitened to impair transparency. Further in this case, poor shaping tends to occur and, on extrusion blow molding, blow moldability becomes worse due to crystallization of the parison.

With the copolyester (A), it is particularly preferred that the content of the triol units (I) and/or triol units (II) be in a range of 0.03 to 0.7 mole % based on the sum of the moles of total diol and triol units, which can provide the resulting copolyester with a sufficiently high melt viscosity and good melt moldability including extrusion blow moldability. In this case, the resulting molded articles are free from whitening or poor shaping and have excellent mechanical strength, and the copolyester itself enjoys high productivity. From the same point of view, it is particularly preferred for the copolyester (B) to have a content of the triol units (I) and/or triol units (II) of 0.05 to 0.5 mole % on the same basis.

Of the copolyesters of the present invention, the copolyester (B) having, as diol units in addition to ethylene glycol units, at least one group of units selected from the group consisting of diol units (III) and diol units (IV), has good impact resistance.

The copolyester (B) of the present invention may contain, together with ethylene glycol units, either one or both of diol units (III) and diol units (IV), and contain as triol units either one or both of triol units (I) and triol units (II). More particularly, the copolyester (B) of the present invention includes, with respect to possession of the diol units (III), diol units (IV), triol units (I) and triol units (II), the following 9 embodiments each having:

① diol units (III) and triol units (I),
② diol units (III) and triol units (II),
③ diol units (IV) and triol units (I),
④ diol units (IV) and triol units (II),
⑤ diol units (III), diol units (IV) and triol units (I),
⑥ diol units (III), diol units (IV) and triol units (II),
⑦ diol units (III), triol units (I) and triol units (II),
⑧ diol units (IV), triol units (I) and triol units (II),
⑨ diol units (III), diol units (IV), triol units (I) and triol units (II).

Among these, the above ① and ② are preferred in view of easiness in producing the polyester (B).

In the diol units (III) and diol units (IV), the group A is a group (ethylene group) represented by formula —CH$_2$CH$_2$— or a group (1,2-propylene group) represented by formula —CH(CH)CH$_2$—. With the copolyester (B) of the present invention and with the diol units (III) and/or diol units (IV) and triol units (I) and/or triol units (II) contained therein, all of the group A may be an ethylene group, all of the group A may be an 1,2-propylene group, or part of the group A may be an ethylene group, with the rest being an 1,2-propylene group. Among these embodiments, it is desirable that the group A in the diol units (III) and/or diol units (IV) and triol units (I) and/or triol units (II) in the copolyester (B) be an ethylene group in view of easiness of production of the copolyester (B) and production cost.

The group B in the diol units (III) is a divalent hydrocarbon group, a carbonyl group, a sulfonyl group, an oxygen atom or a direct bond (—). Where the group B is a divalent hydrocarbon group, the group is desirably an alkylene group or alkylidene group having 1 to 8 carbon atoms or a divalent aromatic group. Examples of desirable divalent hydrocarbon groups are methylene group, ethylene group, ethylidene group, 1,2-propylene group, propylidene group, trimethylene group, isopropylidene group, butylidene group, ethylethylene group, tetramethylene group, 1-methylpropylidene group, 1,2-dimethylethylene group, pentylidene group, 1-methylbutylidene group, pentamethylene group, 1-ethyl-2-methylethylene group, 1,3-dimethyltrimethylene group, 1-ethylpropylidene group, trimethylethylene group, isopropylmethylene group, 1-methylbutylidene group, 2,2-dimethylpropylidene group, hexamethylene group, 1-ethylbutylidene group, 1,2-diethylethylene group, 1,3-dimethylbutylidene group, ethyltrimethylethylene group, heptamethylene group, octamethylene group, 1,1-cyclopentylidene group, 1,1-cyclohexylidene group, 1,1-cycloheptylidene group, 1,1-cyclooctylidene group, benzylidene group and 1-phenylethylidene group.

With the copolyester (B) of the present invention, the group B contained in the diol units (III) and triol units (I) present in the copolyester (B) may be the same or different. Among the above, the group B in the diol units (III) and triol units (I) of the copolyester (B) of the present invention is preferably an isopropylidene group, sulfonyl group and/or 1,1-cyclohexylidene group, which leads to good thermal stability of the copolyester on melting.

With the copolyester (B) of the present invention, j, k, m and n in the diol units (III) and diol units (IV) are each independently an integer of 1 to 8. The j, k, m and n may therefore be the same or different. It is desirable that, in particular, j, k, m and n be each independently an integer of 1 or 2, which ensures good thermal stability of the copolyesters on melting.

Further with the copolyester (B) of the present invention, it is particularly preferred in view of production cost and easiness of production and melt stability of the copolyester (B), that the diol units (III) and diol units (IV) be represented by the following formulas (XI) and (XII), respectively.

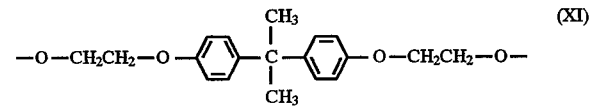

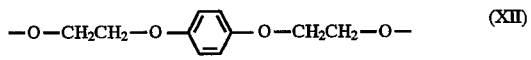

It is necessary that the copolyester (B) of the present invention comprise at least one group of units selected from the group consisting of diol units (III) and diol units (IV) in an amount (when containing both, the total amount thereof) of 1 to 15 mole % based on the sum of the moles of total diol and said triol units (i.e. triol units (I) and/or triol units (II)) constituting the copolyester (B). In other words, the copolyester (B) should contain 1 to 15 moles of diol units (III) and/or diol units (IV) based on 100 moles of the sum of total diol units and the above triol units.

If the diol units (III) and/or diol units (IV) are contained in an amount of less than 1 mole %, the rate of solid phase polymerization on producing copolyester (B) is low.

Besides, the resulting copolyester (B) will have too high a melting point, so that the cycle time becomes long on conducting extrusion blow molding or like melt molding processes, thereby decreasing the productivity on production of molded articles.

On the other hand, if the content of the diol units (III) and/or diol units (IV) exceeds 15 mole %, the polyester prepolymer, which is an intermediate product on production of the copolyester (B), will have too low a melting point or become amorphous, thereby causing such problems as chips of the prepolymer sticking together on preliminary crystallization in the polymerization step or on solid phase polymerization, or the solid phase polymerization itself becoming impossible to conduct. In addition, the resulting copolyester (B) will be colored markedly, so that molded articles obtained therefrom have poor color shade.

It is particularly preferred that the content of the diol units (III) and/or diol units (IV) be in a range of 5 to 10 mole % based on the sum of the moles of total diol and said triol units, which can shorten the cycle of melt molding, in particular extrusion blow molding, ensure good color and mechanical properties such as impact strength and ensure high productivity of solid phase polymerization, with no sticking of polyester prepolymer chips.

The copolyesters of the present invention may as necessary contain, in addition to the above terephthalic acid units, ethylene glycol units, diol units (III), diol units (IV), triol units (I) and triol units (II), not more than 10 mole %, based on the moles of total structural units, of structural units derived from other difunctional compounds. Examples of the structural units derived from such other difunctional compounds are those derived from difunctional groups, e.g. aromatic dicarboxylic acids, such as isophthalic acid, phthalic acid, naphthalenedicarboxylic acid, biphenyldicarboxylic acid, diphenyl ether dicarboxylic acid, diphenyl sulfone dicarboxylic acid, diphenyl ketone dicarboxylic acid and sodium sulfoisophthalate; aliphatic dicarboxylic acids, such as malonic acid, succinic acid, adipic acid, azelaic acid and sebacic acid; alicyclic dicarboxylic acids, such as decalindicarboxylic acid and cyclohexanedicarboxylic acid; hydroxycarboxylic acids, such as glycolic acid, hydroxyacrylic acid, hydroxypropionic acid, quinovic acid, hydroxybenzoic acid and mandelic acid; aliphatic lactones, such as ε-caprolactone; aliphatic diols, such as trimethylene glycol, tetramethylene glycol, hexamethylene glycol, neopentyl glycol, diethylene glycol and polyethylene glycols; aromatic diols, such as hydroquinone, catechol, naphthalene diol, resorcin, bisphenol A and bisphenol S; and alicyclic diols, such as cyclohexane dimethanol. Further, the copolyesters of the present invention may as necessary contain not more than 0.1 mole % based on the total structural units constituting them of units from multi-functional compounds, e.g. multi-valent carboxylic acids, such as trimellitic acid, trimesic acid and tricarballic acid; and polyhydric alcohols, such as trimethylolpropane and pentaerythritol.

The intrinsic viscosity of the copolyesters of the present invention is, depending on the type of melt molding employed, desirably in a range of 0.6 to 1.5 dl/g when they are subjected to melt molding accompanying melt extrusion, in particular extrusion blow molding, and more preferably in a range of 0.9 to 1.4 dl/g, in view of the mechanical strength and appearance and the productivity on producing molded articles. In particular, if the intrinsic viscosity is less than 0.6 dl/g, parisons formed on extrusion blow molding will sag significantly, thereby causing poor shaping and, further, the obtained molded articles will tend to have low mechanical strength.

On the other hand, on conducting molding operations accompanying melt extrusion, in particular on extrusion blow molding, if the copolyesters have an intrinsic viscosity exceeding 1.5 dl/g, the melt viscosity will become too high, so that, on melt extrusion, in particular extrusion blow molding, the molded articles will tend to form weld lines and, further, have poor appearance. Besides, molding problems occur, such as nonuniform throughput due to high torque on the extrusion. Furthermore, the copolyesters having an intrinsic viscosity exceeding 1.5 dl/g require a long time for the extrusion thereof, so that the productivity of molded articles tends to decrease. The above relationship between the intrinsic viscosity of the copolyesters and the moldability thereof and the physical properties of molded articles obtained therefrom appears particularly markedly when they are extrusion blow molded. This relationship is not limited to extrusion blow molding. It is observed on melt moldings accompanying melt extrusion in general, such as extrusion molding and injection-extrusion molding.

The copolyester (A) of the present invention desirably has a melt viscosity ($\eta_1$) at a shear rate of 0.1 rad/sec and at a temperature of 270° C. of $5\times10^4$ to $5\times10^6$ poises. Then, the copolyester (A) will, when melt molded by, for example, extrusion blow molding, cause only little curl-back, thereby almost completely preventing occurrence of poor molding and markedly suppressing melt fracture, die swell and like phenomena. As a result, molded articles having particularly excellent appearance and mechanical properties can be obtained.

The copolyester (A) of the present invention also desirably has a melt viscosity ($\eta_2$) at a shear rate of 100 rad/sec and at a temperature of 270° C. of $5\times10^3$ to $5\times10^5$ poises. Then, the copolyester (A) will, when melt molded by, for example, extrusion blow molding, smoothly prevent extrudates such as parison from deforming by drawdown or drooping, so that the productivity becomes high. Furthermore, the polyester (A) does not undergo thermal decomposition or cause uneven extrusion or occurrence of weld lines.

It is particularly desirable that the copolyester (A) of the present invention satisfy not only the elements of the melt viscosity ($\eta_1$) at a shear rate of 0.1 rad/sec and at a temperature of 270° C. and the melt viscosity ($\eta_2$) at a shear rate of 100 rad/sec and at a temperature of 270° C., but the following condition ①:

$$-0.7 \leq (\tfrac{1}{3})\log_{10}(\eta_2/\eta_1) \leq -0.2 \qquad ①$$

With satisfaction of the above condition ①, the copolyester (A), exhibiting appropriate non-Newtonian behavior shows a moderately low melt viscosity at high shear rates and a moderately high melt viscosity at low shear rates, thereby having excellent formability of parison when subjected to, in particular, extrusion blow molding, injection-extrusion molding or like melt moldings.

To achieve still better formability of parisons, it is more preferred that the value of $(\tfrac{1}{3})\log_{10}(\eta_2/\eta_1)$ in the above formula ① be in a range of −0.60 to −0.25. In the above formula ①, the value $(\tfrac{1}{3})\log_{10}(\eta_2/\eta_1)$ can be obtained as the gradient of a straight line connecting the 2 points of the melt viscosities $\eta_1$ and $\eta_2$ in a log-log graph with the ordinate representing the melt viscosity and the abscissa the shear rate.

The copolyester (B) of the present invention desirably has a melt viscosity ($\eta_3$) at a shear rate of 0.1 rad/sec and at a temperature of 40° C. above the melting point of $5\times10^4$ to $5\times10^6$ poises. Then, the copolyester (B) will, when melt molded by, for example, extrusion blow molding, cause only little curl-back, thereby almost completely preventing occurrence of poor molding and markedly suppressing melt fracture, die swell and like phenomena. As a result, molded articles having particularly excellent appearance and mechanical properties can be obtained.

The copolyester (B) of the present invention also desirably has a melt viscosity ($\eta_4$) at a shear rate of 100 rad/sec and at a temperature of 40° C. above the melting point of $5 \times 10^3$ to $5 \times 10^5$ poises. Then, the copolyester (B) will, when melt molded by, for example, extrusion blow molding, smoothly prevent extrudates such as parison from deforming by drawdown or drooping, so that the productivity becomes high. Furthermore, the polyester (B) does not undergo thermal decomposition or cause uneven extrusion or occurrence of weld lines.

It is particularly desirable that the copolyester (B) of the present invention satisfy not only the elements of the melt viscosity ($\eta_3$) at a shear rate of 0.1 rad/sec and at a temperature 40° C. above the melting point and the melt viscosity ($\eta_4$) at a shear rate of 100 rad/sec and at a temperature 40° C. above the melting point, but the following condition ②:

$$-0.7 \leq (+e, fra\ 3+ee\ )\log_{10}(\eta_4/\eta_3) \leq -0.2 \qquad ②$$

With satisfaction of the above condition ②, the copolyester (B), exhibiting appropriate non-Newtonian behavior, shows a moderately low melt viscosity at high shear rates and a moderately high melt viscosity at low shear rates, thereby having excellent formability of parison when subjected to, in particular, extrusion blow molding, injection-extrusion molding or like melt moldings.

To achieve still better formability of parison, it is more preferred that the value of ($\frac{1}{3}$)$\log_{10}(\eta_4/\eta_3)$ in the above formula ② be in a range of −0.60 to −0.25. In the above formula ②, the value ($\frac{1}{3}$)$\log_{10}(\eta_4/\eta_3)$ can be obtained as the gradient of a straight line connecting the 2 points of the melt viscosities $\eta_3$ and $\eta_4$ in a log-log graph with the ordinate representing the melt viscosity and the abscissa the shear rate.

It is desirable that the copolyesters of the present invention have a glass transition temperature of at least 60° C. It is more preferred that the glass transition temperature be at least 70° C., which prevents more effectively molded articles obtained by extrusion blow molding or like melt moldings from shrinking. With the copolyesters having a glass transition temperature of less than 60° C., the resulting molded articles, in particular extrusion blow molded articles, sometimes shrink after being taken out from dies due to relaxation of residual stress, thereby impairing their appearance.

It is further desirable that the copolyesters of the present invention have a melt flow rate (hereinafter sometimes referred to as "MFR") at a temperature 40° C. above the melting point of 0.3 to 7.5 g/10 min, more preferably 0.5 to 5 g/10 min, from the viewpoint of shapability on melt molding such as extrusion blow molding, the uniformity of obtained molded articles and the productivity on molding.

The above copolyesters of the present invention can be produced in a short period time and at a good productivity by subjecting to esterification or transesterification starting materials consisting essentially of (1) a dicarboxylic acid component consisting essentially of terephthalic acid or ester-forming derivatives thereof, (2) a diol component consisting essentially of ethylene glycol; or a diol component comprising ethylene glycol and a diol component (VII) represented by the above formula (VII) and/or a diol component (VIII) represented by the above formula (VIII) in an amount of about 1 to 15 mole % based on the sum of the moles of total diol and triol components described in (3) below, and (3) a triol component containing a triol component (V) represented by the formula (V) and/or a triol component (VI) represented by the formula (VI), in an amount of about 0.01 to 1 mole % based on the sum of the moles of total diol and triol components;

to form a polyester prepolymer and then solid phase polymerizing the polyester prepolymer.

The above series of reactions can form in the resulting copolyesters the triol units (I) from the triol component (V), the triol units (II) from the triol component (VI), the diol units (III) from the diol component (VII) and the diol units (IV) from the diol component (VIII). Consequently, with the above formulas (V) and (VI) and those (VII) and (VIII) relating to the triol components and the diol components, respectively, the type or substance and the desirable examples of the group A and group B and, further, the details and desirable values of j, k, m, n, p, q, r, s, t and u are as described in detail in the above description for the triol units (I), triol units (II), diol units (III) and diol units (IV) with respect to the group A and group B and j, k, m, n, p, q, r, s, t and u. Preferred examples of the triol components (V) and (VI) are as follows.

Preferred examples of the triol component (V) used for the production of the copolyesters of the present invention are as follows.

REFERENCE NO. 1

2-[4-(2-hydroxyethoxy)phenyl]-2-[3'-(2-hydroxyethyl)-4'-(2-hydroxyethoxy)phenyl]propane (hereinafter sometimes referred to as "HEPP")

REFERENCE NO. 2

2-{4-[2-(2-hydroxyethoxy)ethoxy]phenyl}-2-[3'-(2-hydroxyethyl)-4'-(2-hydroxyethoxy)phenyl]propane

REFERENCE NO. 3

2-[4-(2-hydroxyethoxy)phenyl]-2-{3'-(2-hydroxyethyl)-4'-[2-(2-hydroxyethoxy)ethoxy]phenyl}propane

REFERENCE NO. 4

2-[4-(2-hydroxyethoxy)phenyl]-2-{3'-[2-(2-hydroxyethoxy) ethyl]-4'-(2-hydroxyethoxy)phenyl}propane

REFERENCE NO. 5

2-{4-[2-(2-hydroxyethoxy)ethoxy]phenyl}-2-{3'-(2-hydroxyethyl)-4'-[2-(2-hydroxyethoxy)ethoxy] phenyl}propane

REFERENCE NO. 6

2-{4-[2-(2-hydroxyethoxy)ethoxy]phenyl}-2-{3'-[2-(2-hydroxyethoxy) ethyl]-4'-[2-(2-hydroxyethoxy)ethoxy] phenyl}propane

REFERENCE NO. 7

[4-(2-hydroxyethoxy)phenyl]-[3'-(2-hydroxyethyl)-4'-(2-hydroxyethoxy) phenyl] sulfone

REFERENCE NO. 8

{4-[2-(2-hydroxyethoxy)ethoxy]phenyl}-[3'-(2-hydroxyethyl)-4'-(2-hydroxyethoxy)phenyl] sulfone

REFERENCE NO. 9

[4-(2-hydroxyethoxy)phenyl]-{3'-(2-hydroxyethyl)-4'-[2-(2-hydroxyethoxy)ethoxy]phenyl} sulfone

REFERENCE NO. 10

[4-(2-hydroxyethoxy)phenyl]-{3'-[2-(2-hydroxyethoxy)ethyl]-4'-(2-hydroxyethoxy)phenyl} sulfone

REFERENCE NO. 11

{4-[2-(2-hydroxyethoxy)ethoxy]phenyl}-{3'-(2-hydroxyethyl)-4'-[2-(2-hydroxyethoxy)ethoxy]phenyl} sulfone

REFERENCE NO. 12

{4-[2-(2-hydroxyethoxy)ethoxy]phenyl}-{3'-[2-(2-hydroxyethoxy) ethyl]-4'-[2-(2-hydroxyethoxy)ethoxy]phenyl} sulfone

REFERENCE NO. 13

1-[4-(2-hydroxyethoxy)phenyl]-1-[3'-(2-hydroxyethyl)-4'-(2-hydroxyethoxy)phenyl]cyclohexane

REFERENCE NO. 14

1-{4-[2-(2-hydroxyethoxy)ethoxy]phenyl}-1-[3'-(2-hydroxyethyl)-4'-(2-hydroxyethoxy)phenyl]cyclohexane

REFERENCE NO. 15

1-[4-(2-hydroxyethoxy)phenyl]-1-{3'-(2-hydroxyethyl)-4'-[2-(2-hydroxyethoxy)ethoxy]phenyl}cyclohexane

REFERENCE NO. 16

1-[4-(2-hydroxyethoxy)phenyl]-1-{3'-[2-(2-hydroxyethoxy) ethyl]-4'-(2-hydroxyethoxy) phenyl}cyclohexane

REFERENCE NO. 17

1-{4-[2-(2-hydroxyethoxy)ethoxy]phenyl}-1-{3'-(2-hydroxyethyl)-4'-[2-(2-hydroxyethoxy)ethoxy]phenyl}cyclohexane

REFERENCE NO. 18

1-{4-[2-(2-hydroxyethoxy)ethoxy]phenyl}-1-{3'-[2-(2-hydroxyethoxy) ethyl]-4'-[2-(2-hydroxyethoxy)ethoxy]phenyl}cyclohexane

REFERENCE NO. 19

[4-(2-hydroxyethoxy)phenyl]-[3'-(2-hydroxyethyl)-4'-(2-hydroxyethoxy) phenyl] ether

REFERENCE NO. 20

{4-[2-(2-hydroxyethoxy)ethoxy]phenyl}-[3'-(2-hydroxyethyl)-4'-(2-hydroxyethoxy)phenyl] ether

REFERENCE NO. 21

[4-(2-hydroxyethoxy)phenyl]-{3'-(2-hydroxyethyl)-4-[2'-(2-hydroxyethoxy)ethoxy]phenyl} ether

REFERENCE NO. 22

[4-(2-hydroxyethoxy)phenyl]-{3'-[2-(2-hydroxyethoxy)ethyl]-4'-(2-hydroxyethoxy)phenyl} ether

REFERENCE NO. 23

{4-[2-(2-hydroxyethoxy)ethoxy]phenyl}-{3'-(2-hydroxyethyl)-4'-[2-(2-hydroxyethoxy)ethoxy]phenyl} ether

REFERENCE NO. 24

{4-[2-(2-hydroxyethoxy)ethoxy]phenyl}-{3'-[2-(2-hydroxyethoxy)ethyl]-4'-[2-(2-hydroxyethoxy)ethoxy] phenyl} ether

REFERENCE NO. 25

[4-(2-hydroxyethoxy)phenyl]-[3'-(2-hydroxyethyl)-4'-(2-hydroxyethoxy) phenyl] ketone

REFERENCE NO. 26

{4-[2-(2-hydroxyethoxy)ethoxy]phenyl}-[3'-(2-hydroxyethyl)-4'-(2-hydroxyethoxy)phenyl] ketone

REFERENCE NO. 27

[4-(2-hydroxyethoxy)phenyl]-{3'-(2-hydroxyethyl)-4'-[2'-(2-hydroxyethoxy)ethoxy]phenyl} ketone

REFERENCE NO. 28

[4-(2-hydroxyethoxy)phenyl]-{3'-[2-(2-hydroxyethoxy)ethyl]-4'-(2-hydroxyethoxy)phenyl} ketone

REFERENCE NO. 29

{4-[2-(2-hydroxyethoxy)ethoxy]phenyl}-{3'-(2-hydroxyethyl)-4'-[2-(2-hydroxyethoxy)ethoxy]phenyl} ketone

REFERENCE NO. 30

{4-[2-(2-hydroxyethoxy)ethoxy]phenyl}-{3'-[2-(2-hydroxyethoxy) ethyl]-4'-[2-(2-hydroxyethoxy)ethoxy] phenyl} ketone

REFERENCE NO. 31

4-(2-hydroxyethoxy)-3'-(2-hydroxyethyl)-4'-(2-hydroxyethoxy) biphenyl

REFERENCE NO. 32

4-[2-(2-hydroxyethoxy)ethoxy]-3'-(2-hydroxyethyl)-4'-(2-hydroxyethoxy)biphenyl

REFERENCE NO. 33

4-(2-hydroxyethoxy)-3'-(2-hydroxyethyl)-4'-[2'-(2-hydroxyethoxy) ethoxy]biphenyl

REFERENCE NO. 34

4-(2-hydroxyethoxy)-{3'-[2-(2-hydroxyethoxy)ethoxy]-4'-(2-hydroxyethoxy)phenyl}biphenyl

REFERENCE NO. 35

4-[2-(2-hydroxyethoxy)ethoxy]-3'-(2-hydroxyethyl)-4'-[2-(2-hydroxyethoxy)ethoxy]biphenyl

REFERENCE NO. 36

4-[2-(2-hydroxyethoxy)ethoxy]-3'-[2-(2-hydroxyethoxy)-ethyl]-4'-[2-(2-hydroxyethoxy)ethoxy]biphenyl

REFERENCE NO. 37

2-{4-{2-[2-(2-hydroxyethoxy)ethoxy]ethoxy}phenyl}-2-{3'-(2-hydroxyethyl)-4'-{2-[2-(2-hydroxyethoxy)ethoxy]ethoxy}phenyl}propane

REFERENCE NO. 38

2-{4-{2-[2-(2-hydroxyethoxy)ethoxy]ethoxy}phenyl}-2-{3'-(2-hydroxyethyl)-4'-{2-{2-[2-(2-hydroxyethoxy)ethoxy]ethoxy}ethoxy}phenyl}propane

REFERENCE NO. 39

2-{4-{2-{2-{2-[2-(2-hydroxyethoxy)ethoxy]ethoxy}ethoxy}ethoxy}phenyl}-2-{3'-[2-(2-hydroxyethoxy)ethyl]-4'-{2-{2-[2-(2-hydroxyethoxy)ethoxy]ethoxy}ethoxy}phenyl}propane

REFERENCE NO. 40

{4-{2-[2-(2-hydroxyethoxy)ethoxy]ethoxy}phenyl}-{3'-[2-(2-hydroxyethoxy)ethyl]-4'-{2-[2-(2-hydroxyethoxy)ethoxy]ethoxy}phenyl} sulfone

REFERENCE NO. 41

{4-{2-[2-(2-hydroxyethoxy)ethoxy]ethoxy}phenyl}-{3'-[2-(2-hydroxyethoxy)ethyl]-4'-{2-{2-[2-(2-hydroxyethoxy)ethoxy]ethoxy}ethoxy}phenyl} sulfone

REFERENCE NO. 42

{4-{2-{2-{2-[2-(2-hydroxyethoxy)ethoxy]ethoxy}ethoxy}ethoxy}phenyl}-{3'-{2-{2-[2-(2-hydroxyethoxy)ethoxy]ethoxy}ethyl}-4'-{2-{2-{2-[2(2-hydroxyethoxy]ethoxy}ethoxy}ethoxy}phenyl} sulfone

REFERENCE NO. 43

{4-{2-[2-(2-hydroxyethoxy)ethoxy]ethoxy}phenyl}-{3'-{2-{2-[2-(2-hydroxyethoxy)ethoxy]ethoxy}ethyl}-4'-{2-[2-(2-hydroxyethoxy)ethoxy]ethoxy}phenyl} ether

REFERENCE NO. 44

{4-{2-{2-{2-[2-(2-hydroxyethoxy)ethoxy]ethoxy}ethoxy}ethoxy}phenyl}-{3'-{2-{2-{2-[2-(2-hydroxyethoxy)ethoxy]ethoxy}ethoxy}ethyl}-4'-{2-{2-{2-[2-(2-hydroxyethoxy)ethoxy]ethoxy}ethoxy}ethoxy}phenyl} ether

REFERENCE NO. 45

{4-{2-[2-(2-hydroxyethoxy)ethoxy]ethoxy}phenyl}-{3'-{2-{2-{2-[2-(2-hydroxyethoxy)ethoxy]ethoxy}ethoxy}ethyl}-4'-{2-[2-(2-hydroxyethoxy)ethoxy]ethoxy}phenyl} ketone

REFERENCE NO. 46

{4-[2-(2-hydroxyethoxy)ethoxy]phenyl}-{3'-[2-(2-hydroxyethoxy)ethyl]-4'-{2-{2-[2-(2-hydroxyethoxy)ethoxy]ethoxy}ethoxy}phenyl} ketone

REFERENCE NO. 47

4-(2-hydroxyethoxy)-3'-(2-hydroxyethyl)-4'-{2-[2-(2-hydroxyethoxy)ethoxy]ethoxy}biphenyl

REFERENCE NO. 48

4-{2-{2-{2-[2-(2-hydroxyethoxy)ethoxy]ethoxy}ethoxy}ethoxy}-3'-{2-{2-[2-(2-hydroxyethoxy)ethoxy]ethoxy}ethyl}-4'-[2-(2-hydroxyethoxy)ethoxy]biphenyl Among the above, 2-[4-(2-hydroxyethoxy)phenyl]-2-[3'-(2-hydroxyethyl)-4'-(2-hydroxyethoxy)phenyl]propane is preferably used as the triol component (V), in view of cost and easiness of production, melt stability of the resulting copolyesters and like factors.

Preferred examples of the triol component (VI) used for producing the copolyesters of the present invention are as follows.

REFERENCE NO. 49

1,4-bis(2-hydroxyethoxy)-2-(2-hydroxyethyl)benzene

REFERENCE NO. 50

1,4-bis(2-hydroxyethoxy)-2-[2-(2-hydroxyethoxy)ethyl]benzene

REFERENCE NO. 51

1-(2-hydroxyethoxy)-2-(2-hydroxyethyl)-4-[2-(2-hydroxyethoxy)ethoxy]benzene

REFERENCE NO. 52

1,4-bis[2-(2-hydroxyethoxy)ethoxy]-2-(2-hydroxyethyl)benzene

REFERENCE NO. 53

1-(2-hydroxyethoxy)-2-[2-(2-hydroxyethoxy)ethyl]-4-[2-(2-hydroxyethoxy)ethoxy]benzene

REFERENCE NO. 54

1,4-bis[2-(2-hydroxyethoxy)ethoxy]-2-[2-(2-hydroxyethoxy)ethyl]benzene

REFERENCE NO. 55

1,4-bis{2-[2-(2-hydroxyethoxy)ethoxy]ethoxy}-2-(2-hydroxyethyl)benzene

REFERENCE NO. 56

1-[2-(2-hydroxyethoxy)ethyl]-2-{2-[2-(2-hydroxyethoxy)ethoxy]ethoxy}-5-{2-{2-[2-(2-hydroxyethoxy)ethoxy]ethoxy}ethoxy}benzene

REFERENCE NO. 57

1,4-bis{2-{2-{2-[2-(2-hydroxyethoxy)ethoxy]ethoxy}ethoxy}-2-{2-{2-{2-[2-(2-hydroxyethoxy)ethoxy]ethoxy}ethoxy}ethyl}benzene Among the above, 1,4-bis(2-hydroxyethoxy)-2-(2-hydroxyethyl)benzene is preferably used as the triol component (VI), in view of cost and easiness of production, melt stability of the resulting copolyesters and like factors.

Preferred examples of the diol component (VII) used for producing the copolyester (B) of the present invention are 2,2-bis[4-(2-hydroxyethoxy)phenyl]propane, 2-{4-[2-(2-hydroxyethoxy)ethoxy]phenyl}-2-[4'-(2-hydroxyethoxy)phenyl]propane, 2,2-bis{4-[2-(2-hydroxyethoxy)ethoxy]phenyl}propane, bis[4-(2-hydroxyethoxy)phenyl]sulfone, {4-[2-(2-hydroxyethoxy)ethoxy]phenyl}-[4'-(2-hydroxyethoxy)phenyl]sulfone, bis{4-[2-(2-hydroxyethoxy)ethoxy]phenyl}sulfone, 1,1-bis[4-(2-hydroxyethoxy)phenyl]cyclohexane, 1-{4-[2-(2-hydroxyethoxy)ethoxy]phenyl}-1-[4'-(2-hydroxyethoxy)phenyl]cyclohexane and 1,1-bis{4-[2-(2-hydroxyethoxy)ethoxy]phenyl}cyclohexane.

Among the above, 2,2-bis[4-(2-hydroxyethoxy)phenyl]propane is preferably used as the diol component (VII), in view of cost and easiness of production of the copolyester (B), the melt stability of the resulting copolyester (B) and like factors.

Preferred examples of the diol component (VIII) used for producing the copolyester (B) of the present invention are 1,4-bis(2-hydroxyethoxy)benzene, 1-(2-hydroxyethoxy)-4-[2-(2-hydroxyethoxy)ethoxy]benzene and 1,4-bis[2-(2-hydroxyethoxy)ethoxy]benzene.

Among the above, 1,4-bis(2-hydroxyethoxy)benzene is preferably used as the diol component (VIII), in view of cost and easiness of production of the copolyester (B), the melt stability of the resulting copolyester (B) and like factors.

On the production of the copolyesters of the present invention, components other than the above terephthalic acid component, ethylene glycol, diol component (VII), diol component (VIII), triol component (V) and triol component (VI) may also be as necessary used in combination as long as their amount is not more than 10 mole % based on the moles of total reaction components. Examples of such other components are, as given in the above description of other copolymerization units containable in the copolyesters of the present invention, difunctional groups, e.g. aromatic dicarboxylic acids, such as isophthalic acid, phthalic acid, naphthalenedicarboxylic acid, biphenyldicarboxylic acid, diphenyl ether dicarboxylic acid, diphenyl sulfone dicarboxylic acid, diphenyl ketone dicarboxylic acid, sodium sulfoisophthalate and ester-forming derivatives of the foregoing; aliphatic dicarboxylic acids, such as malonic acid, succinic acid, adipic acid, azelaic acid, sebacic acid and ester-forming derivatives of the foregoing; alicyclic dicarboxylic acids, such as decalindicarboxylic acid, cyclohexanedicarboxylic acid and ester-forming derivatives of the foregoing; hydroxycarboxylic acids, such as glycolic acid, hydroxyacrylic acid, hydroxypropionic acid, quinovic acid, hydroxybenzoic acid, mandelic acid, and ester-forming derivatives of the foregoing; aliphatic lactones, such as ε-caprolactone; aliphatic diols, such as trimethylene glycol, tetramethylene glycol, hexamethylene glycol, neopentyl glycol, diethylene glycol and polyethylene glycols; aromatic diols, such as hydroquinone, catechol, naphthalene diol, resorcin, bisphenol A and bisphenol S; and alicyclic diols, such as cyclohexane dimethanol. Further, there may be as necessary used not more than 0.1 mole % based on the total reaction components of multi-functional compounds, e.g. multivalent carboxylic acids, such as trimellitic acid, trimesic acid, tricarballic acid or ester-forming derivatives of the foregoing; and polyhydric alcohols, such as trimethylolpropane and pentaerythritol.

On production of the copolyester (A), a dicarboxylic acid component consisting essentially of terephthalic acid or ester-forming derivatives thereof is, as described above, subjected to esterification or transesterification with a diol component consisting essentially of ethylene glycol and a triol component [i.e. triol component (V) and/or triol component (VI)], to form a low-polymerization-degree compound. On this occasion, it is recommended to mix the reaction components such that the molar ratio of (total diol components):(total dicarboxylic acid components) becomes 1.1:1 to 1.5:1 and that the molar ratio of (triol component) :(total dicarboxylic acid components) is 0.01:100 to 1:100.

On production of the copolyester (B), a dicarboxylic acid component consisting essentially of terephthalic acid or ester-forming derivatives thereof is, as described above, subjected to esterification or transesterification with a diol component consisting essentially of ethylene glycol and further containing a diol component (VII) and/or diol component (VIII) and a triol component [i.e. triol component (V) and/or triol component (VI)], to form a low-polymerization-degree compound. On this occasion, it is recommended to mix the reaction components such that the molar ratio of (total diol components):(total dicarboxylic acid components) becomes 1.1:1 to 1.5:1 and that the molar ratio of (triol component):(total dicarboxylic acid components) is 0.01:100 to 1:100.

It is also recommended to carry out the above esterification or transesterification, generally, under atmospheric pressure to an absolute pressure of about 3 kg/cm$^2$ and at a temperature of 230° to 280° C., while distilling off the water or alcohol that is formed. After the reaction, additives such as polycondensation catalyst and coloring preventing agent may be added as necessary and then melt polycondensation is conducted, generally, under a reduced pressure of not more than 5 mmHg and at a temperature of 200° to 280° C. until a polyester prepolymer having the desired viscosity is obtained. On this occasion, the polyester prepolymer desirably has an intrinsic viscosity of 0.40 to 0.80 dl/g and an MFR exceeding 15.0 g/10 min, in view of handleability and like factors.

Where a polycondensation catalyst is used for the above melt polycondensation, the catalyst may be any one generally used for producing polyesters. Examples of the catalyst are antimony compounds, e.g. antimony oxide; germanium compounds, e.g. germanium oxide; titanium compounds, e.g. tetramethoxytitanium, tetraethoxytitanium, tetra-n-propoxytitanium, tetraisopropoxytitanium and tetrabutoxytitanium; and tin compounds, e.g. di-n-butyltin dilaurate, di-n-butyltin oxide and dibutyltin diacetate. These catalysts may be used singly or in combination of 2 or more. With use of a polycondensation catalyst, its amount is desirably in a range of 0.002 to 0.8% by weight based on the weight of the dicarboxylic acid component.

Where a coloring preventing agent is used, there can be used phosphorus compounds, e.g. phosphorous acid, phosphoric acid, trimethyl phosphite, triphenyl phosphite, tridecyl phosphite, trimethyl phosphate, tridecyl phosphate and triphenyl phosphate. These phosphorus compounds may be used singly or in combination of 2 or more. With use of a coloring preventing agent comprising any one of the above phosphorus compounds, its amount is desirably in a range of 0.001 to 0.5% by weight based on the weight of the dicarboxylic acid component.

It is recommended, in order to suppress coloring of copolyesters due to thermal decomposition, to add a manganese compound such as manganese acetate, in an amount of about 0.001 to 0.5% by weight based on the weight of the dicarboxylic acid component, more preferably 0.05 to 0.3% by weight on the same basis.

It is also desirable to conduct the above esterification or transesterification and/or melt polycondensation in the presence of a diethylene glycol byproduction-suppressing agent, e.g. tetraalkylammonium hydroxides such as tetraethylammonium hydroxide and organic amines such as triethanolamine and triethylamine.

Then, the polyester prepolymer obtained by the above polycondensation is formed into chips or pellets having a dice-, cylindrical or any optional shape, which are, after being pre-dried at a temperature of generally not more than 190° C., subjected to solid phase polymerization until the intrinsic viscosity, MFR and like indexes reach the desired values, to yield the desired copolyester. The solid phase polymerization is desirably conducted under vacuum or a reduced pressure or under an atmosphere of an inert gas such as nitrogen. It is desirable, during the solid phase polymerization, to move, by appropriate means such as a tumbling process or a gas fluidized bed process, the chips or pellets of the polyester prepolymer, in order that they will not stick together. The solid phase polymerization is desirably conducted generally at a temperature of 180° to 240° C., more preferably 210° to 240° C. Furthermore, it is recommended to set the temperature for the solid phase polymerization at, within the above range, at least 15° C., preferably at least 20° C. lower than the melting point of the copolyester to prevent sticking between chips or pellets. The solid phase polymerization is desirably conducted for, generally, about 5 to 40 hours in view of productivity and the like.

Carrying out the above series of processes can produce the copolyesters of the present invention in a short period of time and at a high productivity.

The copolyesters of the present invention can be molded by extrusion blow molding, injection-extrusion molding, extrusion molding, injection molding or like melt molding processes, with good moldability, into various molded articles. The molded articles obtained by these melt molding processes can produce, with good productivity and smoothly, shaped articles having excellent dimensional precision, transparency, heat resistance, moisture resistance, chemical resistance and similar properties.

The copolyesters of the present invention have a high melt viscosity and melt viscosity characteristics suitable for, among the above melt molding processes, particularly melt molding processes accompanying melt extrusion process, especially extrusion blow molding. On extrusion blow molding with the copolyesters of the present invention, parisons extruded have a good drawdown property, so that the drawdown time is maintained within a suitable range and the parisons have a uniform diameter. Besides, a good blow moldability is achieved without causing problems on molding, thereby producing hollow molded articles having good shape and dimensional precision smoothly and with good productivity. The obtained hollow molded articles can yield extrusion blow molded articles having excellent transparency, heat resistance, moisture resistance, chemical resistance and like properties.

Furthermore, the copolyesters of the present invention having the above features are suitably used for producing large-size hollow shaped articles via relatively long parisons having a length of at least 20 cm.

Melt molding of the copolyesters of the present invention can be conducted following conventional procedures for each of melt molding processes used for thermoplastic resins in general, e.g. extrusion blow molding, injection-extrusion molding, extrusion molding and injection molding, and is not particularly limited with respect to actual content or conditions of procedure. In particular, on extrusion blow molding of the copolyesters of the present invention, the type of extrusion blow molding is not specifically limited. That is, in the same manner as in known extrusion blow molding, the copolyesters of the present invention can be melt extrusion molded into cylindrical parisons, which are, while being in a softened state, inserted into a die for blowing and then air or like gases is blown into the die to swell the parisons into the desired hollow shapes defined by the shape of the die cavity. In this case, it is desirable to adjust the melt extrusion temperature within a range of (melting point of copolyester +10° C.) to (melting point of copolyester +70° C.), in view of moldability.

The shaped articles of the present invention may be of any shape, with no specific limitation, and they can assume, according to each use, the shape of, for example, a hollow article, tube, plate, sheet, film, rod and die. The shaped articles may have any size with no specific restrictions. Among these, the present invention is particularly suitably applied to hollow articles obtained by extrusion blow molding.

Further, the shaped articles obtained from the copolyesters of the present invention may be formed of the copolyesters alone or have the shape of laminates with other plastics, metals, fibers, fabrics or like other materials, or may be of a shape other than laminates, in combination with the above other materials. In particular, where the shaped articles of the present invention are extrusion blow molded articles, they can be formed into single-layer hollow articles (e.g. hollow containers) comprising the copolyesters of the present invention only or multilayer hollow articles formed of the copolyesters of the present invention in combination with other plastics such as polyethylene, polypropylene, ethylenevinyl alcohol copolymer or polyethylene terephthalate (PET). More particularly, 3-layer bottles having a construction of PET layer/the copolyester layer/PET layer, and 5-layer bottles with PET layer/the copolyester layer/PET layer/the copolyester layer/PET layer may be made. The shaped articles of the present invention are, however, not limited to these examples.

The copolyesters of the present invention may, as necessary, incorporate other thermoplastic resins and various additives conventionally used for polyester resins in general, e.g. coloring agents such as dyes and pigments, stabilizers such as UV absorbers, antistatic agents, flame retardants, flame retardant auxiliaries, lubricants, plasticizers and inorganic fillers.

The aromatic triols represented by the general formula (V) can be produced by feeding an appropriate bisphenol into an air-tight vessel and treating it, under pressure and in the presence of catalytic amount of a base, with an excess amount of an alkylene oxide. The reaction temperature is preferably in a range of 70° to 250° C., more preferably in a range of 80° to 230° C. The reaction time, which depends on the reaction temperature, is generally in a range of about 5 to about 10 hours. The alkylene oxide used is preferably in an amount of about 4 to 15 molar equivalents based on the bisphenol. The reaction is desirably carried out in a solvent.

Examples of the bisphenol used in the above reaction, which suitably correspond to the general formula (V), bisphenol A (4,4'-isopropylidene diphenol), bisphenol S([bis (4-hydroxyphenyl) sulfone], bis(4-hydroxyphenyl) ether, bis (4-hydroxyphenyl) ketone and 4,4'-dihydroxybiphenyl. Examples of usable alkylene oxides are ethylene oxide and propylene oxide. Examples of the base, which acts as a reaction catalyst, are inorganic bases, e.g. potassium carbonate, sodium carbonate, sodium methylate, sodium ethylate, sodium hydroxide and potassium hydroxide, and amine-based bases, e.g. triethylamine, trimethylamine and tributylamine.

The aromatic triols represented by the general formula (VI) can be produced by, in the above production process for the aromatic triols represented by the general formula (V), following the same procedure except for changing the bisphenol to a hydroquinone.

The aromatic triols represented by the general formula (VI) can be also produced by condensing by a known process a starting material 2,5-dihydroxyphenylacetic acid (homogentisic acid) with an ethylene halohydrin or propylene halohydrin in the presence of a base catalyst, and reducing the carboxylic group with a reducing agent.

Examples of the ethylene halohydrin and propylene halohydrin used in the above reaction are ethylene chlorohydrin, ethylene bromohydrin, propylene chlorohydrin and propylene bromohydrin, among which ethylene bromohydrin and propylene bromohydrin are preferred in view of reactivity. The same bases as used for producing the aromatic triols represented by the general formula (V) are also usable here. Examples of the reducing agent are metal hydrides, e.g. aluminum lithiumhydride, aluminum tri(t-butoxy)hydride and sodium borohydride, among which aluminum lithiumhydride is preferred in view of reactivity and economy.

The aromatic triols thus obtained are as necessary purified by any known process, such as recrystallization or column chromatography, to achieve higher purity.

The aromatic triols are useful as crosslinking agents and resin-modifying agents. For instance, on production of a polycondensed polymer such as polyesters, polyurethanes or polycarbonates, previously mixing an aromatic triol according to the present invention as copolymerization monomer into the starting material mixture and subjecting the resulting mixture to polycondensation can provide crosslinked polymers in which the 3 hydroxyl groups contained in the aromatic triol form ester bonds, urethane bonds or carbonate bonds. Modification of polyesters with an aromatic triol according to the present invention enables the resulting polyesters to have good extrusion blow moldability.

EXAMPLES

Other features of the invention will become more apparent in the course of the detailed descriptions of exemplified embodiments which are given for illustration of the invention and are not intended to be limiting thereof. In the Examples and Comparative Examples that follow, the determination of the structure and purity of aromatic triols, the content of each of the structural units and properties of polyesters (copolyesters or homopolyesters) and evaluations of the drawdown tendency and blow moldability of parisons on extrusion blow molding of polyesters and the transparency and impact resistance of molded articles (bottles) obtained by the extrusion blow molding were carried out in accordance with the following methods.

(1) Structure of aromatic triol

Identified by 500 MHz-NMR (made by JEOL) spectrometry with a solvent of deuterated chloroform. In the Examples, the values of chemical shift, peak shape and number of protons read from an NMR chart are shown.

(2) Purity of aromatic triol

Determined by calculating the ratio between the peak area of compound sample and the total peak area present on the chromatogram obtained by a liquid chromatography with a methanol/water mixed solvent as mobile phase.

For the liquid chromatography, there were used System Controller SCL-6B, Chromatopack C-R4AX, a spectrophotometer for ultraviolet and visible region SPE-6A (all made by Shimazu Corporation), and Shim-Pack CLC-ODS (M) as column (made by Shimadzu Corporation, inner dia.: 4.6 mm×250 mm). The detection wavelength was set at 254 nm.

(3) Content of each structural unit in polyester

Polyester sample was subjected to methanolysis and constituting structural components are separated by high-performance liquid chromatography. The components obtained were each subjected to quantitative determination by infrared absorption (IR) spectrometry to give the content of each component. The content values were identified by $^1$H-NMR spectrometry with a solvent of deuterated trifluoroacetic acid.

(4) Intrinsic viscosity of polyester

Determined by measurements on 1/1 by weight mixed solvent of phenol and tetrachloroethane with Ubelohde viscosimeter (HRK-3, made by Hayashi Seisakusho) at 30° C.

(5) Melt flow rate (MFR) of prepolymer or polyester

Measured with Melt Indexer L244 (made by Takara Kogyo KK). Particularly, a cylinder having an inner diameter of 9.5 mm and a length of 162 mm was filled with chips of a prepolymer or polyester (final product) sample, which were melted at 270° C. The melt was uniformly loaded with a 2,160-g plunger having a diameter of 9.48 mm and the flowout rate (g/10 min) of the prepolymer or polyester extruded through a 2.1 mm-dia. orifice was measured and taken as the melt flow rate.

(6) Melt viscosities ($\eta_1, \eta_2, \eta_3$ and $\eta_4$) of polyester

The melt viscosity at a shear rate of 0.1 rad/sec ($\eta_1$ or $\eta_3$) at a temperature of 270° C. or (melting point +40° C.) and that at a shear rate of 100 rad/sec ($\eta_2$ or $\eta_4$) at a temperature of 270° C. or (melting point +40° C.) were dynamically measured with a mechanical spectrometer (RMS-800, made by Reometrics Co.).

(7) Glass transition temperature (Tg) and melting point (Tm) of polyester

Measured in accordance with JIS K7121 by differential scanning calorimeter (DSC) with a thermal analysis system (Mettler TA3000) at a rate of 10° C./min.

(8) Drawdown tendency of parison on extrusion blow molding (i) Drawdown time (sec) of parison Sample was extruded through an extrusion blow molding machine (hollow molding machine, Type TB-ST-6P, made by Suzuki Iron Works) at an extrusion temperature of 270° C. through an annular orifice into a cylindrical parison. The cylindrical parison was, while being in a softened state, cut and bottom-formed by pinching with a blow die, and the cuts were then blow molded into bottles (designed capacity: 1,000 ml, designed wall thickness: 0.4 mm) for soft drinks. The above extrusion blow molding machine used here was so designed as to pinch off with die and blow at a time point where the parison sagged by 25 cm. The time required for 25-cm drawdown was thus measured and taken as the drawdown time.

With the extrusion blow molding machine used here, drawdown times within a range of 10 to 25 seconds showed good moldability and those, in particular, within a range of 15 to 25 seconds still better moldability. Drawdown times of less than 10 seconds, meaning severe drawdown, cause the parison to assume a nonuniform shape, and such a parison becomes, after blowing, defective with a large thickness dispersion, becomes impossible to insert into blow dies and causes clogging at its hollow part. On the other hand, with the drawdown time exceeding 25 seconds, the productivity of shaped articles (bottles) decreases and the polyester, having too high a melt viscosity, cannot be blown uniformly. Further in this case, unbonding at the pinch-off part of bottles, generation of weld lines and breakage of the molding machine due to increased torque tends to occur.

(ii) Difference between the maximum and minimum diameters of parison

Polyester sample was extruded with the above extrusion blow molding machine at a temperature of 270° C. into a cylindrical parison, and the parison was, when its length reached 25 cm, measured for the maximum diameter (outer diameter) and minimum diameter (inner diameter), from which the difference was obtained.

The annular die of the extrusion nozzle of the above extrusion blow molding machine used here was 3.5 cm. The parison extruded therethrough tends to be attenuated as it goes apart from the die, due to drawdown as caused by its self-weight. A difference between the maximum and minimum diameters of a parison ensures, generally, smooth extrusion blow molding operation. On the other hand, if the difference exceeds 1 cm, the parison will, after blowing, generate thickness unevenness, thereby producing defectives or, in extreme cases, clog and become unblowable.

(iii) Overall evaluation of drawdown tendency of parison

Overall evaluation of drawdown tendency of parison was made in terms of the drawdown time, the difference between the maximum and minimum diameters of parison and the productivity of bottles, in accordance with the criteria shown in Table 1 below. On this occasion, the productivity of bottles was judged good, from the cost factor, when at least 120 pieces of bottles was producible with less than 10 pieces of defectives in 100 pieces. The defective herein means that there occurred at least one problem selected from the group consisting of:

a) Extruded parison cannot be inserted into blow die due to drawdown;
b) Parison clogs at its hollow part;
c) Unbonding at the pinch-off part due to high viscosity; and
d) Deformation or breakage of bottle due to nonuniform blow.

TABLE 1

Criteria of overall evaluation of parison drawdown tendency
O (good): satisfies all of the following conditions (a) Draw-down time is in a range of 15 to 25 seconds.
(b) Difference between the maximum and minimum diameters of parison is not more than 1 cm.
(c) Production of bottles is at least 120 pieces per hour and defective bottles are less than 10 pieces in 100 pieces.

Δ (marginal): satisfies any one of the following conditions (a) Draw-down time is at least 10 seconds and less than 15 seconds, or is more than 25 seconds and not more than 60 seconds.
(b) Difference between the maximum and minimum diameters of parison is more than 1 cm and not more than 2 cm.
(c) Production of bottles is at least 60 pieces and less than 120 pieces per hour and defective bottles are at least 10 pieces and less than 30 pieces in 100 pieces.

X (bad): satisfies any one of the following conditions (a) Draw-down time is less than 10 seconds or exceeds 60 seconds.
(b) Difference between the maximum and minimum diameters of parison exceeds 2 cm.
(c) Production of bottles is less 60 pieces per hour and defective bottles are in at least 30 pieces in 100 pieces.

(9) Blow moldability on extrusion blow molding
(i) Average wall thickness of bottle A bottle obtained by molding was divided from the top down to the bottom into 10 pieces, each of which was then divided into 4 pieces at the same pitch in the circumferential direction of bottle. On the total of 40 pieces the wall thicknesses were measured and the average of 40 measurements calculated. The average wall thickness is desirably in a range of 0.25 to 0.55 mm from the viewpoint of appearance, tactility and bottle strength.

(ii) Thickness unevenness of bottle

Of the wall thicknesses of bottle body part obtained in the above measurement (i), the difference between the maximum and minimum thicknesses was obtained for evaluation.

The thickness difference is desirably less than 0.15 mm, because otherwise very thin and/or broken parts are generated, so that appearance and/or tactility become poor.

(iii) Overall evaluation of blow moldability

Conducted in accordance with the evaluation criteria shown in Table 2 below.

TABLE 2

Overall evaluation criteria for blow moldability

| | |
|---|---|
| O (good): | Average wall thickness is in a range of 0.25 to 0.55 mm and thickness unevenness is less than 0.15 mm. |
| X (bad): | Average wall thickness is less than 0.25 mm or exceeds 0.55 mm, or thickness unevenness is at least 0.15 mm. |

(10) Transparency of bottle
(i) Haze value

The body of bottle was divided, from the top, middle down to bottom, into 6 parts, which were then each divided into 4 pieces in the circumferential direction into 24 pieces. They were tested with an integrating sphere type light transmittance-total light reflectance tester (SEP-HS 3OD-R type, made by Nihon Seimitsu Kogaku KK) for haze value at each piece. The average of the 24 measurements was taken as the haze value of bottle. With a haze value exceeding 8, the transparency becomes poor due to whitening by generation of spherulites or light scattering by gel-like agglomerates. The haze value is desirably not more than 4, which ensures good transparency. (ii) b-value The body of bottle was cut to small pieces (square piece of 1 cm×1 cm), which were measured with a color difference meter (SM-4, made by Suga Instruments KK) by reflection method. With the b-value exceeding 8, the bottle shows a yellowish tone and becomes of poor appearance. The b-value is desirably not more than 4 in view of color tone.

(iii) Overall evaluation of bottle transparency

Conducted in accordance with the evaluation criteria shown in Table 3 below.

TABLE 3

Overall evaluation criteria for transparency of bottle

| | |
|---|---|
| O (good): | Haze value is not more than 4 and b-value is not more than 4. |
| Δ (mar-ginal) | Haze value exceeds 4 and is not more than 8, or b-value exceeds 4 and is not more than 8. |
| X (bad): | Haze value exceeds 8, or b-value exceeds 8. |

(11) Impact resistance of bottle

Bottle sample was filled with distilled water and sealed by fitting a stopper. After being allowed to stand at a temperature of 0° C. for 24 hours, the bottle was dropped from the height of 50 cm onto a flat, concrete floor, straight with the bottom down. This test was repeated 5 times on the same bottle and the results were evaluated in accordance with the criteria shown in Table 4 below.

TABLE 4

Evaluation criteria of impact resistance of bottle

| | |
|---|---|
| O (good): | No cracks or splits generated after 5 tests. |
| Δ (mar-: ginal) | Although no cracks or splits generated at the first test, they generated at any one of the second through fifth test. |
| X (bad): | Cracks or splits generated already at the first test. |

Example 1 (Synthesis of HEPP)

An airtight reaction vessel was charged with a starting material bisphenol of bisphenol A (114 parts by weight, 0.5 mole), to which 70 parts of toluene and triethylamine (1.0 part by weight, 0.01 mole) were added. After the air in the vessel had been replaced by nitrogen under a pressure of 0.7 kg/cm², ethylene oxide (110 parts by weight, 2.5 moles) was added and reaction was effected, while the temperature was elevated from 80° C. to 210° C., for 5 hours. The reaction was further continued at 200° C. for 2 hours. The reaction mixture was allowed to cool and the pressure decreased, and then hydrochloric acid added 50 parts by weight). The resulting reaction mixture was condensed, and isolated and purified by column chromatography, to yield 23.4 parts by weight of HEPP (yield based on bisphenol: 13%).

¹H-NMR (CDCl) δ: 1.67 (s, CH₃, 3H), 1.68 (s, CH₃, 3H), 2.40 (b, OH, 1H), 2.88 (t, CH₂, 2H), 3.77 (t, CH₂, 2H), 3.90 (m, CH₂, 4H), 4.10 (m, CH₂, 4H), 6.70–7.15 (m, aromatic ring, 7H)

Example 2 (synthesis of compound of Reference No. 7) and Example 3 (Synthesis of compound of Reference No. 49)

Example 1 was repeated except that the type and amount fed of the starting material compound was changed as shown in Table 5, to obtain aromatic triols corresponding to starting materials. The results are also shown in Table 5.

Compound of Reference No. 7

¹H-NMR (CDCl₃) δ: 2.35 (b, OH, 1H), 2.88 (t, CH₂, 2H), 3.76 (t, CH₂, 2H), 3.92 (m, CH₂, 4H), 4.15 (m, CH₂, 4H), 6.60–7.18 (m, aromatic ring, 7H)

Compound of Reference No. 49

¹H-NMR (CDCl₃) δ: 1.22 (t, OH, 1H), 1.54 (m, OH, 1H), 2.95 (t, CH₂, 2H), 3.60 (m, OH, 1H), 3.87 (t, CH₂, 2H), 3.88 (m, CH₂, 4H), 4.05 (m, CH₂, 4H), 6.75–7.00 (m, aromatic ring, 3H)

Example 4 (Synthesis of compound of Reference No. 49)

Homogentisic acid (84.1 parts by weight, 0.5 mole) was dissolved in 100 parts by weight of acetone, and 150 parts by weight of potassium carbonate was added to the solution. To the reaction mixture, which was being stirred, ethylene bromohydrin (189 parts by weight, 1.5 moles) was added gently, and the resulting mixture was heated to 60° C. to effect reaction for 5 hours. From the obtained reaction mixture the potassium carbonate was removed by filtration. The filtrate was, after being condensed, purified by column chromatography, to yield a condensate of homogentisic acid and ethylene bromohydrin (purity: 99.0%). The condensate was dissolved in 200 parts by weight of anhydrous tetrahydrofuran, and 300 ml of aluminum lithium hydride (1 mole/1 solution in tetrahydrofuran) was added dropwise with stirring at −50° C. While the reaction temperature was allowed to elevate up to near room temperature, reaction was effected for 5 hours. Thereafter, 300 parts by weight of methanol was added to the reaction mixture to quench the unreacted aluminum lithium hydride. A large excess of diethyl ether and water were added to the reaction mixture and the organic layer was condensed. The obtained mixture was isolated and purified by column chromatography, to yield 110.1 parts by weight of compound of Reference No. 49 (yield based on homogentisic acid: 91%). The results are shown in Table 5.

¹H-NMR (CDCl₃) δ: 1.21 (t, OH, 1H), 1.57 (m, OH, 1H), 2.95 (t, CH₂, 2H), 3.57 (m, OH, 1H), 3.88 (m, CH₂, 2H), 3.88 (m, CH₂, 4H), 4.03 (m, CH₂, 4H), 6.75–7.00 (m, aromatic ring, 3H)

TABLE 5

| | Example 1 | Example 2 | Example 3 | Example 4 |
|---|---|---|---|---|
| Reference number | 1 (HEPP) | 7 | 49 | 49 |
| Starting material compound | Biophenol A | Biophenol S | Hydro-quinone | Homogen-tisic acid |
| Weight fed (g) | 114 | 125 | 55.1 | 84.1 |
| Yield (%) | 13 | 11 | 15 | 91 |
| Purity (%) | 99.5 | 99.3 | 99.8 | 99.9 |

Example 5

(1) A slurry was prepared from 100.00 parts by weight of terephthalic acid, 44.83 parts by weight of ethylene glycol and 0.108 part by weight of 2-[4-(2-hydroxyethoxy)phenyl]-2-[3'-(2-hydroxyethyl)-4'-(2-hydroxyethoxy)phenyl]propane (HEPP) represented by the following formula (XIII).

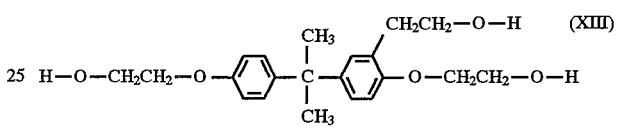

To the slurry, 0.020 part by weight of germanium dioxide, 0.015 part by weight of phosphorus acid, 0.015 part by weight of manganese acetate and 0.015 part by weight of tetraethylammonium hydroxide were added. The resulting slurry was heated, under a pressure (absolute pressure: 2.5 kg/cm²), to a temperature of 250° C., to conduct esterification to an esterification ratio of 95%, to produce a low-polymerization-degree compound. The compound thus obtained was, under a reduced pressure of 1 mmHg and at a temperature of 270° C., melt polycondensed, to yield a copolyester prepolymer having an intrinsic viscosity of 0.70 dl/g. The prepolymer was extruded through a nozzle into a strand, which was then cut into cylindrical chips (diameter: 2.5 mm, length: 3.5 mm). The prepolymer had an MFR of 35 g/10 min.

The copolyester prepolymer chips thus obtained were, after being pre-dried at a temperature of 150° C. for 5 hours, subjected to solid phase polymerization under a reduced pressure of 0.1 mmHg at 225° C. (28° C. lower than the melting point) for 31 hours, to yield a high molecular copolyester.

(2) The copolymer obtained in the above (1) was tested for the content of each structural units by the afore-described method. The content of terephthalic acid units, ethylene glycol units, HEPP units or diethylene glycol units was as shown in Table 7.

(3) The copolymer obtained in the above (1) was tested for the physical properties in accordance with the afore-described methods, to show, as shown in Table 7 below, an intrinsic viscosity of 1.25 dl/g, an MFR at 270° C. of 2.4 g/10 min and melt viscosities at the same temperature and at a shear rate of 0.1 rad/sec ($\eta_1$) and at a shear rate of 100 rad/sec ($\eta_2$) of $1.47 \times 10_5$ poises and $2.30 \times 10_4$ poises, respectively, which led to a value of ($\frac{1}{3}$)log₁₀($\eta_2/\eta_1$) of −0.27.

The copolyester was further tested for Tg and Tm by the afore-described method, to show 78° C. and 253° C. respectively, as shown in Table 7 below.

(4) The copolyester was extrusion blow molded through an extrusion blow molding machine (hollow molding machine TB-ST-6P, made by Suzuki Iron Works) into bottles (designed capacity: 1,000 ml, designed wall thickness: 0.4 mm). The obtained parison was tested for drawdown tendency and blow moldability, and the bottles for transparency, in accordance with the afore-described methods, to give the results shown in Table 10 below.

Examples 6 and 7

Example 5 was repeated except that the type and amount of diol component and triol component and the temperature and time of solid phase polymerization were changed as shown in Table 7 below, to conduct esterification, melt polycondensation and solid phase polymerization, to produce copolyesters. The copolyesters obtained were tested for the content of structural units and the physical properties in the same manner. The results are shown in Table 7 below.

The copolyesters obtained in these Examples 6 and 7 were extrusion blow molded in the same manner into bottles. The drawdown tendency and blow moldability of the parisons, which were intermediate products, and the transparency of the obtained bottles were determined or evaluated by the afore-described methods. The results are shown in Table 10 below.

Examples 8 through 10

Example 5 was repeated except that the type and amount of diol component and triol component and the temperature and time of solid phase polymerization were changed as shown in Table 8 below, to conduct esterification, melt polycondensation and solid phase polymerization, to produce copolyesters. The copolyesters obtained were tested for the content of structural units and the physical properties in the same manner. The results are shown in Table 8 below.

The copolyesters obtained in these Examples 8 through 10 were extrusion blow molded in the same manner into bottles. The drawdown tendency and blow moldability of the parisons, which were intermediate products, and the transparency of the obtained bottles were determined or evaluated by the afore-described methods. The results are shown in Table 10 below.

Comparative Examples 1 through 4

(1) Example 5 was repeated except that the type and amount of diol component and triol component and the temperature and time of solid phase polymerization were changed as shown in Table 9 below, to conduct esterification, melt polycondensation and solid phase polymerization, to produce copolyesters (Comparative Examples 1 through 3) and a homopolyester (Comparative Example 4). The copolyesters and homopolyester obtained were tested for the content of structural units and the physical properties in the same manner. The results are shown in Table 9 below.

On this occasion, the copolyester obtained in Comparative Example 3, which had a low melting point, was tested for MFR and intrinsic viscosities at a shear rate of 0.1 rad/sec ($\eta_1$) and at a shear rate of 100 rad/sec ($\eta_2$) were all tested at 240° C.

(2) The copolyesters and homopolyesters obtained in these Comparative Examples 1 through 4 were extrusion blow molded in the same manner into bottles (however, the copolyester obtained in Comparative Example 3, which had a low melting point, was at first melt extruded at 240° C and then blow molded). The drawdown tendency and blow moldability of the parisons, which were intermediate products, and the transparency of the obtained bottles were determined or evaluated by the afore-described methods. The results are shown in Table 10 below.

(3) On the above extrusion blow molding (2), the copolyesters obtained in Comparative Examples 1 and 2, having a large content of triol units, gave parisons whitened during drawdown due to generation of spherulites. These parisons cause, on molding into bottles, whitening or breakage of bottom part, thereby being unable to be blown uniformly. Furthermore, the obtained bottles, generating gel-like agglomerates at the transparent part of body, had markedly poor appearance.

In Comparative Example 3, where cyclohexane dimethanol had been copolymerized, the obtained copolyester had a decreased melting point and hence, in spite of low-temperature molding, caused markedly severe drawdown on extrusion blow molding, thus being of poor moldability.

In Comparative Example 4, bottles could not be produced due to severe drawdown on extrusion blow molding.

The coding used in the above Examples 5 through 10 and the following Tables 7 through 9 are as shown in Table 6 below.

TABLE 6

| Code | Compound |
|---|---|
| TPA | Terephthalic acid |
| EG | Ethylene glycol |
| CHDM | 1,4-cyclohexane dimethanol |
| HEPP | 2-[4-(2-hydroxyethoxy)phenyl]-2-[3'-(2-hydroxyethyl)-4'-(2-hydroxyethoxy)phenyl]propane (compound represented by the above formula (XIII) |
| HEB | 1,4-bis(2-hydroxyethoxy)-2-(2-hydroxyethyl)benzene (compound represented by the following formula (XIV) |
| DEG | Diethylene glycol |

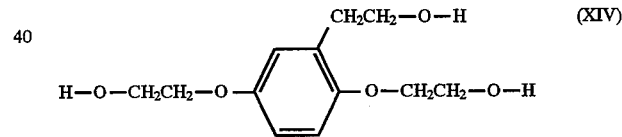

(XIV)

TABLE 7

| | Example 5 | Example 6 | Example 7 |
|---|---|---|---|
| Starting mat'l component | | | |
| Dicarboxylic acid component | | | |
| Type: parts by weight | TPA: 100 | TPA: 100 | TPA: 100 |
| Diol component | | | |
| Type | EG | EG | EG |
| Parts by weight | 44.83 | 44.83 | 44.83 |
| Triol component | | | |
| Type | HEPP | HEPP | HEPP |
| Parts by weight | 0.108 | 0.108 | 0.108 |
| Prepolymer | | | |
| Intrinsic viscosity (dl/g) | 0.70 | 0.68 | 0.69 |
| MFR (g/10 min) | 35 | 31 | 29 |

TABLE 7-continued

|  | Example 5 | Example 6 | Example 7 |
|---|---|---|---|
| Solid phase polymerization |  |  |  |
| temperature | 225 | 225 | 225 |
| time | 31 | 23 | 16 |
| Copolyester [structural unit] Dicarboxylic acid units |  |  |  |
| From | TPA | TPA | TPA |
| Mole % | 100 | 100 | 100 |
| Diol units |  |  |  |
| From | EG | EG | EG |
| Mole %[1) | 97.15 | 97.10 | 96.75 |
| From | DEG | DEG | DEG |
| Mole %[1) | 2.80 | 2.75 | 3.00 |
| Triol units |  |  |  |
| From | HEPP | HEPP | HEPP |
| Mole % | 0.05 | 0.15 | 0.25 |
| [Physical properties] |  |  |  |
| Intrinsic viscosity (dl/g) | 1.25 | 1.12 | 1.11 |
| MFR (g/10 min) | 2.4 | 1.9 | 1.5 |
| $\eta_1$ ($10^5$ poises) | 1.47 | 2.28 | 2.90 |
| $\eta_2$ ($10^4$ poises) | 2.30 | 2.20 | 1.90 |
| (1/3) $\log_{10}$ ($\eta_2/\eta_1$) | −0.27 | 0.34 | −0.39 |
| Tg (°C.) | 78 | 78 | 79 |
| Tm (°C.) | 253 | 252 | 252 |

[1)based on sum of total diol units and total triol units.

TABLE 8

|  | Example 8 | Example 9 | Example 10 |
|---|---|---|---|
| Starting mat'l component Dicarboxylic acid component |  |  |  |
| Type: parts by weight | TPA: 100 | TPA: 100 | TPA: 100 |
| Diol component |  |  |  |
| Type | EG | EG | EG |
| Parts by weight | 44.83 | 44.83 | 44.83 |
| Triol component |  |  |  |
| Type | HEPP | HEB | HEB |
| Parts by weight | 1.085 | 0.219 | 0.365 |
| Prepolymer |  |  |  |
| Intrinsic viscosity (dl/g) | 0.66 | 0.69 | 0.67 |
| MFR (g/10 min) | 25 | 24 | 18 |
| Solid phase polymerization |  |  |  |
| temperature | 220 | 225 | 225 |
| time | 8 | 20 | 12 |
| Copolyester [structural unit] Dicarboxylic acid units |  |  |  |
| From | TPA | TPA | TPA |
| Mole % | 100 | 100 | 100 |

TABLE 8-continued

|  | Example 8 | Example 9 | Example 10 |
|---|---|---|---|
| Diol units |  |  |  |
| From | EG | EG | EG |
| Mole %[1) | 96.80 | 97.35 | 96.90 |
| From | DEG | DEG | DEG |
| Mole %[1) | 2.70 | 2.50 | 2.85 |
| Triol units |  |  |  |
| From | HEPP | HEB | HEB |
| Mole % | 0.50 | 0.15 | 0.25 |
| [Physical properties] |  |  |  |
| Intrinsic viscosity (dl/g) | 1.09 | 1.05 | 1.07 |
| MFR (g/10 min) | 0.8 | 2.9 | 2.2 |
| $\eta_1$ ($10^5$ poises) | 5.36 | 1.35 | 2.82 |
| $\eta_2$ ($10^4$ poises) | 1.40 | 1.50 | 2.10 |
| (1/3) $\log_{10}$ ($\eta_2/\eta_1$) | −0.53 | −0.32 | −0.38 |
| Tg (°C.) | 79 | 78 | 79 |
| Tm (°C.) | 251 | 252 | 252 |

[1)based on sum of total diol units and total triol units.

TABLE 9

|  | Comp. Ex. 1 | Comp. Ex. 2 | Comp. Ex. 3 |  | Comp. Ex. 4 |
|---|---|---|---|---|---|
| Starting mat'l component Dicarboxylic acid component |  |  |  |  |  |
| Type: parts by weight | TPA: 100 | TPA: 100 | TPA: 100 |  | TPA: 100 |
| Diol component |  |  |  |  |  |
| Type | EG | EG | EG | CHDM | EG |
| Parts by weight | 44.83 | 44.83 | 44.83 | 4.70 | 44.83 |
| Triol component |  |  |  |  |  |
| Type | HEPP | HEB | — |  | — |
| Parts by weight | 10.848 | 7.291 |  |  |  |
| Prepolymer |  |  |  |  |  |
| Intrinsic viscosity (dl/g) | 0.52 | 0.49 | 0.70 |  | 0.70 |
| MFR (g/10 min) | 13 | 16 | 24 |  | 35 |
| Solid phase polymerization |  |  |  |  |  |
| temperature | 215 | 215 | 200 |  | 225 |
| time | 3 | 2 | 72 |  | 58 |
| Copolyester [structural unit] Dicarboxylic acid units |  |  |  |  |  |
| From | TPA | TPA | TPA |  | TPA |
| Mole % | 100 | 100 | 100 |  | 100 |
| Diol units |  |  |  |  |  |
| From | EG | EG | EG | CHDM | EG |
| Mole %[1) | 92.10 | 92.25 | 90.30 | 6.90 | 97.70 |
| From | DEG | DEG | DEG |  | DEG |
| Mole %[1) | 2.90 | 2.75 | 2.80 |  | 2.30 |
| Triol units |  |  |  |  |  |
| From | HEPP | HEB | — |  | — |
| Mole % | 5.00 | 5.00 |  |  |  |

TABLE 9-continued

|  | Comp. Ex. 1 | Comp. Ex. 2 | Comp. Ex. 3 | Comp. Ex. 4 |
|---|---|---|---|---|
| [Physical properties] | | | | |
| Intrinsic viscosity (dl/g) | 1.03 | 1.01 | 1.08 | 1.05 |
| MFR (g/10 min) | 0.2 | 0.4 | 5.9 | 8.5 |
| $\eta_1$ ($10^5$ poises) | 24.5 | 13.8 | 0.31 | 0.19 |
| $\eta_2$ ($10^4$ poises) | 1.10 | 0.89 | 0.88 | 0.85 |
| (⅓) $\log_{10}$ ($\eta_2/\eta_1$) | −0.78 | −0.73 | −0.18 | −0.12 |
| Tg (°C.) | 78 | 78 | 76 | 78 |
| Tm (°C.) | 245 | 245 | 225 | 253 |

[1])based on sum of total diol units and total triol units.

TABLE 10

Results of extrusion blow molding

| | Drawdown tendency of parison | | | Blow moldability | | | Transparency of bottle | | |
|---|---|---|---|---|---|---|---|---|---|
| | Drawdown time (sec) | Difference between max. and min. diameters[1]) (cm) | Overall evaluation | Average wall thickness (mm) | Thickness unevenness (mm) | Overall evaluation | Haze value | b-value | Overall evaluation |
| Example 5 | 15 | 0.8 | o | 0.35 | 0.1 | o | 1.7 | 1 | o |
| Example 6 | 17 | 0.4 | o | 0.40 | 0.05 | o | 1.9 | 0 | o |
| Example 7 | 19 | 0.3 | o | 0.45 | 0.05 | o | 2.3 | 1 | o |
| Example 8 | 22 | 0.1 | o | 0.50 | 0.05 | o | 2.8 | 1 | o |
| Example 9 | 16 | 0.5 | o | 0.35 | 0.05 | o | 1.7 | 0 | o |
| Example 10 | 19 | 0.3 | o | 0.45 | 0.05 | o | 2.0 | 1 | o |
| Comp. Ex. 1 | 38 | 0.1 | Δ | 0.70 | 0.25 | x | 9.5 | 4.8 | x |
| Comp. Ex. 2 | 32 | 0.1 | Δ | 0.65 | 0.3 | x | 10.5 | 4.5 | x |
| Comp. Ex. 3 | 9 | 2.5 | x | 0.25 | 0.3 | x | 5.6 | 5 | Δ |
| Comp. Ex. 4 | 5 | 2.9 | x | — | — | — | — | — | — |

[1])Difference between the maximum and minimum diameters of parison.

The following is understood from Tables 7 through 10.

The copolyesters of Examples 5 through 10, utilizing HEPP or HEB, either of which is a triol component (V) or a triol component (VI), in amounts in the range specified in the present invention, and thus containing triol units [triol units (I) and/or triol units (II)] derived from these components, all have excellent melt moldability, in particular extrusion blow moldability. In any of the Examples, on producing bottles by extrusion blow molding, the drawdown time of extruded parison is in a range of 15 to 25 seconds, the difference between the maximum and minimum diameters of parisons is not more than 1 cm, the production of bottles is at least 120 pieces per hour with the defectives being less than 10 pieces per 100 pieces, the obtained bottles having an average wall thickness of 0.25 to 0.55 mm, thus proving excellent blow moldability, and the bottles have a haze value of not more than 3 and a b-value of not more than 1, thus proving excellent transparency.

On the other hand, the copolyester of Comparative Example 1, although containing units [triol units (I)] from HEPP, which is a triol component (V), containing them in too large an amount beyond the range specified in the present invention; and the copolyester of Comparative Example 2, although containing units [triol units (II)] from HEB, which is a triol component (VI), containing them in too large an amount beyond the range specified in the present invention, both have too high a melt viscosity ($\eta_1$) and hence have a drawdown time exceeding 25 seconds, are poor in the productivity on extrusion blow molding, and give bottles having too large an average wall thickness and large thickness unevenness and poor transparency.

The copolyester of Comparative Example 3, containing neither triol units (I) or triol units (II) but, instead, units from cyclohexane dimethanol (CHDM) have a low melting point of 225° C. and, although extrusion blow molded at a low temperature (240° C.) have a short drawdown time of 9 seconds, thus proving severe drawdown, thereby having poor extrusion blow moldability. Besides, the obtained bottles have a larger thickness unevenness as compared with Examples 5 through 10 and are also inferior in transparency.

The homopolyester of the Comparative Example 4, containing neither triol units (I) or triol units (II) and corresponding to conventional polyethylene terephthalate, is, as stated in the afore-described item of "Description of prior art", difficult to process by extrusion blow molding in practice.

Example 11

(1) A slurry was prepared from 100.00 parts by weight of terephthalic acid, 44.83 parts by weight of ethylene glycol, 9.52 parts by weight of 2, 2-bis[4-(2-hydroxyethoxy)phenyl] propane represented by the following formula (XV) (hereinafter referred to as "EOBPA")

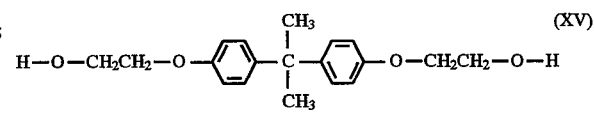

(XV)

and 0.108 part by weight of 2-[4-(2-hydroxyethoxy)phenyl] -2-[3'-(2-hydroxyethyl)-4'-(2-hydroxyethoxy)phenyl] propane represented by the afore-described formula (XIII). To the slurry, 0.020 part by weight of germanium dioxide, 0.015 part by weight of phosphorus acid, 0.015 part by weight of manganese acetate and 0.015 part by weight of tetraethylammonium hydroxide were added. The resulting slurry was heated, under a pressure (absolute pressure: 2.5 kg/cm$^2$), to a temperature of 250° C., to conduct esterification to an esterification ratio of 95%, to produce a low-polymerization-degree compound. The compound thus obtained was, under a reduced pressure of 1 mmHg and at a temperature of 270° C., melt polycondensed, to yield a copolyester prepolymer having an intrinsic viscosity of 0.70 dl/g. The prepolymer was extruded through a nozzle into a strand, which was then cut into cylindrical chips (diameter: 2.5 mm, length: 3.5 mm). The prepolymer had an MFR of 36 g/10 min.

The copolyester prepolymer chips thus obtained were, after being pre-dried at a temperature of 150° C. for 5 hours, subjected to solid phase polymerization under a reduced pressure of 0.1 mmHg at a temperature (about 205° C.) of about 25° C. lower than the melting point for 29 hours, to yield a high molecular copolyester.

(2) The copolymer obtained in the above (1) was tested for the content of each structural units by the afore-described method. The content of terephthalic acid units, ethylene glycol units, EOBPA units, HEPP units or diethylene glycol units was as shown in Table 12.

(3) The copolymer obtained in the above (1) was tested for the physical properties in accordance with the afore-described methods, to show, as shown in Table 12 below, an intrinsic viscosity of 1.21 dl/g, an MFR at a temperature of (melting point +40° C.) (269° C.) of 1.1 g/10 min and melt viscosities at the same temperature and at a shear rate of 0.1 rad/sec ($\eta_3$) and $2.52 \times 10^4$ poises, respectively, which led to a value of $(\frac{1}{3})\log_{10}(\eta_4/\eta_3)$ of $-0.24$.

The copolyester was further tested for Tg and Tm by the afore-described method, to show 78° C. and 229° C. respectively, as shown in Table 12 below.

(4) The copolyester was extrusion blow molded through an extrusion blow molding machine (hollow molding machine TBST-6P, made by Suzuki Iron Works) into bottles (designed capacity: 1,000 ml, designed wall thickness: 0.4 mm). The obtained parison was tested for drawdown tendency and blow moldability, and the bottles for transparency and impact resistance, in accordance with the afore-described methods, to give the results shown in Table 15 below.

Examples 12 through 14

Example 11 was repeated except that the type and amount of diol component and triol component and the temperature and time of solid phase polymerization were changed as shown in Table 12 below, to conduct esterification, melt polycondensation and solid phase polymerization, to produce copolyesters. The copolyesters obtained were tested for the content of structural units and the physical properties in the same manner. The results are shown in Table 12 below.

The copolyesters obtained in these Examples 12 through 14 were extrusion blow molded in the same manner into bottles. The drawdown tendency and blow moldability of the parisons, which were intermediate products, and the transparency and impact resistance of the obtained bottles were determined or evaluated by the afore-described methods. The results are shown in Table 15 below.

Examples 15 through 17

Example 11 was repeated except that the type and amount of diol component and triol component and the temperature and time of solid phase polymerization were changed as shown in Table 13 below, to conduct esterification, melt polycondensation and solid phase polymerization, to produce copolyesters. The copolyesters obtained were tested for the content of structural units and the physical properties in the same manner. The results are shown in Table 13 below.

The copolyesters obtained in these Examples 15 through 17 were extrusion blow molded in the same manner into bottles. The drawdown tendency and blow moldability of the parisons, which were intermediate products, and the transparency and impact resistance of the obtained bottles were determined or evaluated by the afore-described methods. The results are shown in Table 15 below.

Comparative Examples 5 through 9

(1) Example 11 was repeated except that the type and amount of diol component and triol component and the temperature and time of solid phase polymerization were changed as shown in Table 14 below, to conduct esterification, melt polycondensation and solid phase polymerization, to produce copolyesters (Comparative Examples 5 through 8) and a homopolyester (Comparative Example 9). The copolyesters and homopolyester obtained were tested for the content of structural units and the physical properties in the same manner. The results are shown in Table 14 below.

On this occasion, the copolyester obtained in Comparative Example 7, which was amorphous, was tested for MFR and intrinsic viscosities at a shear rate of 0.1 rad/sec ($\eta$) and at a shear rate of 100 rad/sec ($\eta_4$) were all tested at 240° C.

(2) The copolyesters and homopolyesters obtained in these Comparative Examples 5 through 9 were extrusion blow molded in the same manner into bottles. The drawdown tendency and blow moldability of the parisons, which were intermediate products, and the transparency and impact resistance of the obtained bottles were determined or evaluated by the afore-described methods. The results are shown in Table 15 below.

(3) On the above extrusion blow molding (2), in Comparative Example 6, the parison became, during sagging, whitened due to generation of spherulites. The parison caused, on molding into bottles, whitening or breakage of bottom part, thereby being unable to be blown uniformly. Furthermore, the obtained bottles, generating gel-like agglomerates at the transparent part of body, had markedly poor appearance.

In Comparative Example 7, the copolyester obtained by melt polycondensation, which was amorphous, could not be solid phase polymerized. Table 14 below therefore gives the physical properties of the copolyester prepolymer obtained by melt polycondensation and also, while the copolyester prepolymer was extrusion blow molded at a temperature of 240° C., the results of evaluation for the drawdown tendency and blow moldability of the parison on the blow molding and the transparency and impact resistance of the obtained bottles.

In Comparative Example 9, bottles could not be produced due to severe drawdown on extrusion blow molding.

The coding used in the above Examples 11 through 17 and the following Tables 12 through 14 are as shown in Table 11 below.

TABLE 11

| Code | Compound |
| --- | --- |
| TPA | Terephthalic acid |
| EG | Ethylene glycol |
| EOBPA | 2,2-bis[4-(2-hydroxyethoxy)phenyl]propane (compound represented by the above formula (XV) |

TABLE 11-continued

| Code | Compound |
|---|---|
| BHEB | 1,4-bis(2-hydroxyethoxy)benzene (compound represented by the following formula (XVI) |
| CHDM | 1,4-cyclohexane dimethanol |
| HEPP | 2-[4-(2-hydroxyethoxy)phenyl]-2-[3'-(2-hydroxyethyl)-4'-(2-hydroxyethoxy)phenyl]propane (compound represented by the above formula (XIII) |
| HEB | 1,4-bis(2-hydroxyethoxy)-2-(2-hydroxyethyl)benzene (compound represented by the above formula (XIV) |
| DEG | Diethylene glycol |

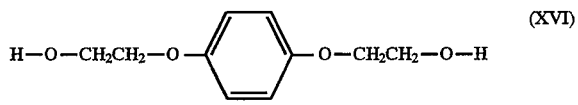

(XVI)

TABLE 12

| | Ex. 11 | Ex. 12 | Ex. 13 | Ex. 14 |
|---|---|---|---|---|
| Starting mat'l component Dicarboxylic acid component | | | | |
| Type: pts by wt. Diol component | TPA: 100 | TPA: 100 | TPA: 100 | TPA: 100 |
| Type | EG | EG | EG | EG |
| Parts by weight | 48.83 | 48.83 | 48.83 | 48.83 |
| Type | EOBPA | EOBPA | EOBPA | EOBPA |
| Parts by weight | 9.52 | 9.52 | 9.52 | 15.24 |
| Triol component | | | | |
| Type | HEPP | HEPP | HEPP | HEPP |
| Parts by weight | 0.108 | 0.325 | 0.651 | 0.325 |
| Prepolymer | | | | |
| Intrinsic viscosity (dl/g) | 0.70 | 0.70 | 0.69 | 0.70 |
| MFR (g/10 min) | 36 | 32 | 28 | 33 |
| Solid phase polymerization | | | | |
| temperature (°C.) | 205 | 205 | 205 | 195 |
| time (hr) | 29 | 23 | 18 | 19 |
| Copolyester [structural unit] Dicarboxylic acid units | | | | |
| From | TPA | TPA | TPA | TPA |
| Mole % | 100 | 100 | 100 | 100 |
| Diol units | | | | |
| From | EG | EG | EG | EG |
| Mole %[1] | 92.35 | 92.05 | 92.05 | 89.10 |
| From | EOBPA | EOBPA | EOBPA | EOBPA |
| Mole %[1] | 5.00 | 5.00 | 5.00 | 8.00 |
| From | DEG | DEG | DEG | DEG |
| Mole %[1] | 2.60 | 2.80 | 2.65 | 2.75 |
| Triol units | | | | |
| From | HEPP | HEPP | HEPP | HEPP |
| Mole % | 0.05 | 0.15 | 0.30 | 0.15 |
| [Physical properties] | | | | |
| Intrinsic viscosity (dl/g) | 1.21 | 1.14 | 1.06 | 1.18 |

TABLE 12-continued

| | Ex. 11 | Ex. 12 | Ex. 13 | Ex. 14 |
|---|---|---|---|---|
| MFR (g/10 min) | 1.1 | 1.4 | 2.2 | 0.7 |
| $\eta_3$ ($10^5$ poises) | 1.32 | 1.81 | 3.01 | 2.90 |
| $\eta_4$ ($10^4$ poises) | 2.52 | 1.79 | 1.04 | 2.23 |
| (⅓) $\log_{10}$ ($\eta_4/\eta_3$) | −0.24 | −0.33 | −0.49 | −0.37 |
| Tg (°C.) | 78 | 78 | 78 | 79 |
| Tm (°C.) | 229 | 228 | 228 | 219 |

[1] based on sum of total diol units and total triol units.

TABLE 13

| | Example 15 | Example 16 | Example 17 |
|---|---|---|---|
| Starting mat'l components Dicarboxylic acid component | | | |
| Type: pts by wt. by weight Diol component | TPA: 100 | TPA: 100 | TPA: 100 |
| Type | EG | EG | EG |
| Parts by weight | 48.83 | 48.83 | 48.83 |
| Type | EOBPA | BHEB | BHEB |
| Parts by weight | 19.05 | 5.97 | 9.55 |
| Triol component | | | |
| Type | HEPP | HEB | HEB |
| Parts by weight | 0.434 | 0.146 | 0.292 |
| Prepolymer | | | |
| Intrinsic viscosity (dl/g) | 0.70 | 0.70 | 0.69 |
| MFR (g/10 min) | 30 | 34 | 33 |
| Solid phase polymerization | | | |
| temperature (°C.) | 190 | 200 | 195 |
| time (hr) | 15 | 32 | 25 |
| Copolyester [structural unit] Dicarboxylic acid units | | | |
| From | TPA | TPA | TPA |
| Mole % | 100 | 100 | 100 |
| Diol units | | | |
| From | EG | EG | EG |
| Mole %[1] | 87.20 | 92.00 | 89.25 |
| From | EOBPA | BHEB | BHEB |
| Mole %[1] | 10.00 | 5.00 | 8.00 |
| From | DEG | DEG | DEG |
| Mole %[1] | 2.60 | 2.90 | 2.55 |
| Triol units | | | |
| From | HEPP | HEB | HEB |
| Mole % | 0.20 | 0.10 | 0.20 |
| [Physical properties] | | | |
| Intrinsic viscosity (dl/g) | 1.10 | 1.22 | 1.12 |
| MFR (g/10 min) | 1.7 | 1.8 | 2.3 |
| $\eta_3$ ($10^5$ poises) | 2.41 | 1.60 | 2.04 |
| $\eta_4$ ($10^4$ poises) | 1.41 | 1.60 | 1.22 |
| (⅓) $\log_{10}$ ($\eta_4/\eta_3$) | −0.41 | −0.33 | −0.41 |
| Tg (°C.) | 80 | 79 | 79 |
| Tm (°C.) | 213 | 227 | 219 |

[1] based on sum of total diol units and total triol units.

TABLE 14

|  | Comp. Ex. 5 | Comp. Ex. 6 | Comp. Ex. 7 | Comp. Ex. 8 | Comp. Ex. 9 |
|---|---|---|---|---|---|
| Starting mat'l components Dicarboxylic acid component | | | | | |
| Type: pts by wt. | TPA: 100 | TPA: 100 | TPA: 100 | TPA: 100 | TPA: 100 |
| Diol component | | | | | |
| Type | EG | EG | EG | EG | EG |
| Parts by weight | 44.83 | 44.83 | 44.83 | 44.83 | 44.83 |
| Type | EOBPA | EOBPA | EOBPA | CHDM | |
| Parts by weight | 9.52 | 9.52 | 57.14 | 4.70 | |
| Triol component | | | | | |
| Type | — | HEPP | HEPP | — | — |
| Parts by weight | | 6.509 | 0.434 | | |
| Prepolymer | | | | | |
| Intrinsic viscosity (dl/g) | 0.70 | 0.61 | 0.69 | 0.70 | 0.68 |
| MFR (g/10 min) | 35 | 24 | 18 | 24 | 36 |
| Solid phase polymerization | | | | | |
| temperature (°C.) | 205 | 195 | — | 200 | 225 |
| time (hr) | 43 | 8 | — | 72 | 58 |
| Copolyester [structural unit] Dicarboxylic acid units | | | | | |
| From | TPA | TPA | TPA | TPA | TPA |
| Mole % | 100 | 100 | 100 | 100 | 100 |
| Diol units | | | | | |
| From | EG | EG | EG | EG | EG |
| Mole %[1) | 92.20 | 89.05 | 67.10 | 90.30 | 97.40 |
| From | EOBPA | EOBPA | EOBPA | CHDM | |
| Mole %[1) | 5.00 | 5.00 | 30.0 | 6.90 | |
| From | DEG | DEG | DEG | DEG | DEG |
| Mole %[1) | 2.80 | 2.95 | 2.70 | 2.80 | 2.60 |
| Triol units | | | | | |
| From | — | HEPP | HEPP | — | — |
| Mole % | | 3.00 | 0.20 | | |
| [Physical properties] | | | | | |
| Intrinsic viscosity (dl/g) | 1.21 | 1.15 | 0.69 | 1.08 | 1.02 |
| MFR (g/10 min) | 6.5 | 0.1 | 18 | 5.9 | 10.5 |
| $\eta_3$ ($10^5$ poises) | 0.221 | 11.8 | 0.068 | 0.310 | 0.120 |
| $\eta_4$ ($10^4$ poises) | 1.63 | 0.85 | 0.37 | 0.880 | 0.610 |
| (⅓) $\log_{10}$ ($\eta_4/\eta_3$) | −0.04 | −0.71 | −0.09 | −0.18 | −0.10 |
| Tg (°C.) | 79 | 79 | 81 | 76 | 78 |
| Tm (°C.) | 228 | 218 | — | 225 | 253 |

[1)based on sum of total diol units and total triol units.

TABLE 15

Results of extrusion blow molding

| | Drawdown tendency of parison | | | Blow moldability | | | Transparency of bottle | | | Impact resistance of bottle |
|---|---|---|---|---|---|---|---|---|---|---|
| | Drawdown time (sec) | Difference between max. and min. diameters[1] (cm) | Overall evaluation | Average wall thickness (mm) | Thickness unevenness (mm) | Overall evaluation | Haze value | b-value | Overall evaluation | |
| Example 11 | 16 | 0.8 | o | 0.35 | 0.1 | o | 1.5 | 1 | o | o |
| Example 12 | 18 | 0.7 | o | 0.40 | 0.01 | o | 2.0 | 1 | o | o |
| Example 13 | 24 | 0.3 | o | 0.50 | 0.05 | o | 2.4 | 2 | o | o |
| Example 14 | 24 | 0.3 | o | 0.50 | 0.05 | o | 1.7 | 2 | o | o |
| Example 15 | 21 | 0.5 | o | 0.45 | 0.05 | o | 1.5 | 3 | o | o |
| Example 16 | 17 | 0.8 | o | 0.40 | 0.1 | o | 1.9 | 1 | o | o |
| Example 17 | 20 | 0.5 | o | 0.45 | 0.05 | o | 2.1 | 1 | o | o |
| Comp. Ex. 5 | 9 | 2.2 | x | 0.25 | 0.30 | x | 2.0 | 1 | Δ | Δ |
| Comp. Ex. 6 | 41 | 0.1 | Δ | 0.65 | 0.25 | x | 8.4 | 2 | x | x |
| Comp. Ex. 7 | 6 | 2.7 | x | 0.15 | 0.20 | x | 2.4 | 6 | Δ | x |
| Comp. Ex. 8 | 9 | 2.5 | x | 0.25 | 0.30 | x | 5.6 | 5 | Δ | Δ |
| Comp. Ex. 9 | 4 | 2.9 | x | — | — | — | — | — | — | — |

[1]Difference between the maximum and minimum diameters of parison.

The following is understood from the above Tables 12 through 15.

The copolyesters of Examples 11 through 17, utilizing EOBPA or BHEB, either of which is a diol component (VII) or a diol component (VIII), and HEPP or HEB, either of which is a triol component (V) or a triol component (VI), in amounts in the range specified in the present invention, and thus containing diol units [diol units (III) or diol units (IV) derived from these diol components and triol units [triol units (I) and/or triol units (II)] derived from these triol component, all have excellent melt moldability, in particular extrusion blow moldability. In all of the Examples, on producing bottles by extrusion blow molding, the drawdown time of extruded parison is in a range of 10 to 25 seconds, the difference between the maximum and minimum diameters of parison is not more than 1 cm, the production of bottles is at least 120 pieces per hour with the defectives being less than 10 pieces per 100 pieces, the obtained bottles having an average wall thickness of 0.25 to 0.55 mm, thus proving excellent blow moldability, the bottles have a haze value of not more than 4 and a b-value of not more than 4, thus proving excellent transparency, and the above results of 5 dropping tests are good.

On the other hand, the copolyester of Comparative Example 5, although containing structural units [diol units (III)] from EOBPA, which is a diol component (VII), but containing no triol units (I) or triol units (II); the copolyester of Comparative Example 6, although containing structural units [diol units (III)] from EOBPA, which is a diol component (VII) and structural units [triol units (I)] from HEPP, which is a triol component (V), but containing the latter in too large an amount beyond the range specified in the present invention; the copolyester of Comparative Example 7, although containing structural units [diol units (III)]from EOBPA, which is a diol component (VII) and structural units [triol units (I)] from HEPP, which is a triol component (V), but containing the former in too large an amount beyond the range specified in the present invention; and the copolyester of Comparative Example 8, containing alicyclic diol units (i.e. diol units from CHDM), which differ from diol units (III) or diol units (IV); are all not applicable to melt molding, in particular extrusion blow molding. These copolyesters all give extruded parisons being poor in both drawdown tendency and blow moldability and all give bottles being inferior in transparency and impact resistance.

The homopolyester of the Comparative Example 9, containing no diol units (III), diol units (IV), triol units (I) or triol units (II) is, as stated in the afore-described item of "Description of prior art", difficult to process by extrusion blow molding in practice.

Example 18

(Preparation of a modified polyester using as crosslinking component the HEPP obtained in Example 1)

A slurry was prepared from 100.00 parts by weight of terephthalic acid, 44.84 parts by weight of ethylene glycol, 0.54 parts by weight (0.25 mole based on terephthalic acid) of HEPP. To the slurry, 1.8 part by weight (150 ppm based on the theoretical amount of polyester produced) of germanium dioxide and 0.95 part by weight (100 ppm based on the theoretical amount of polyester produced) of phosphorus acid were added. The resulting slurry was heated, under a pressure (absolute pressure: 2.5 kg/cm$^2$), to a temperature of 250° C., to conduct esterification to an esterification rate of 95%, to produce a low-polymerization-degree compound. The compound thus obtained was, under a reduced pressure of 0.3 mmHg and at a temperature of 270° C., melt polycondensed, to yield a copolyester prepolymer having an intrinsic viscosity of 0.70 dl/g. The prepolymer was extruded through a nozzle into a strand, which was then cut into cylindrical chips (diameter: 2.5 mm, length: 3.5 mm).

The prepolymer chips thus obtained were, after being predried at a temperature of 150° C. for 5 hours, subjected to solid phase polymerization under a reduced pressure of 0.1 mmHg at a temperature of 225° C. for 6 hours, to yield a high molecular modified polyester.

The modified polyester obtained had an intrinsic viscosity of 1.15 dl/g, a melt flow rate at a temperature of 270° C. of 1.2 g/10 min and a melt viscosity at the same temperature and at a shear rate of 0.1 rad/sec of 210,000 poises.

The modified polyester was heat pressed at 270° C. into a transparent film having a thickness of 100 microns. The transparent film was observed for its appearance and the result is shown in Table 16.

The modified polyester was also evaluated for extrusion blow moldability. With an extrusion blow molding machine (TB-ST-6P, made by Suzuki Iron Works), the modified polyester was extruded through an annular orifice into a parison. The parison was, while being in a softened state, pinched with a blow molding die to cut the mouth part and bond the bottom part, and then blow molded into hollow containers having a capacity of 1,000 ml and an average wall thickness of 0.4 mm. The moldability and the conditions of the hollow containers were evaluated in accordance with the following criteria. The results are shown in Table 16.

○: Extruded parison forms a cylinder having a uniform diameter, and the obtained hollow containers are excellent in smoothness and transparency.

Δ: Although extruded parison forms a cylinder having a uniform diameter, the obtained hollow containers have, showing gel-like agglomerates, poor appearance.

×: Extruded parison does not form a cylinder having a uniform diameter and has some difficulty in giving hollow containers because of frequent occurrence of closure at the hollow part of the parison in a softened state. The obtained hollow containers, carrying gel-like agglomerates, have poor appearance.

Comparative Examples 10 and 11

Example 18 was repeated except that the type and amount used of the crosslinking component was changed as shown in Table 16, to obtain modified polyesters and transparent films formed therefrom. Evaluation of the extrusion blow moldability was conducted in the same manner as in Example 18. The results are shown in Table 16.

In Comparative Examples 10 and 11, it took a longer time for the polyesters to achieve the desired degree of polymerization than in Example 18. The transparent films were markedly poor in appearance, that is, in surface smoothness, neatness and lack of luster, due to the presence of gel-like agglomerates matter. Also in molding test of hollow containers by extrusion blow molding, the containers had markedly poor appearance due to generation of gel-like agglomerates.

As is apparent from Table 16, the polyethylene terephthalate modified by the aromatic triol of the present invention has a higher rate of polymerization and has a more effective suppressed generation of gels and agglomerates, as compared with polyethylene terephthalate modified with a conventional crosslinking agent. It is also understood that the polyethylene terephthalate modified by the aromatic triol of the present invention has better extrusion moldability and gives molded articles having better appearance as compared with polyethylene terephthalate modified with a conventional crosslinking agent.

TABLE 16

| | Example 18 | Comp. Ex. 10 | Comp. Ex. 11 |
|---|---|---|---|
| Crosslinking component | HEPP | Trimethylol-propane | Trimellitic acid |
| Ditto (part by weight) | 0.54 | 0.13 | 0.29 |
| Molar fraction to terephthalic acid (mole %) | 0.25 | 0.25 | 0.25 |
| Intrinsic viscosity of pre-polymer (dl/g) | 0.70 | 0.71 | 0.70 |
| Time required for solid phase polymerization | 6.5 | 8 | 9.5 |
| Intrinsic viscosity (dl/g) | 1.15 | 1.18 | 1.15 |
| Melt flow rate (g/10 min) | 1.2 | 1.1 | 1.4 |
| Melt viscosity (poises) | 210,000 | 222,000 | 170,000 |
| Film appearance | Good. (no gel) | Gels seen. | Gels seen. |
| Extrusion blow moldability and evaluation of hollow container | ○ | Δ | × |

Obviously, numerous modifications and variations of the present invention are possible in the light of the above teachings. It is therefore to be understood that in light of the above teachings, the invention may be practiced otherwise than as specifically described herein.

What is claimed as new and desired to be secured by Letters Patent of the United States is:

1. A copolyester comprising:
   (i) diol units consisting essentially of ethylene glycol units and dicarboxylic acid units consisting essentially of terephthalic acid units,
   said copolyester further comprising:
   (ii) at least one group of triol units selected from the group consisting of:
      (a) triol units (I) each represented by the following formula (I)

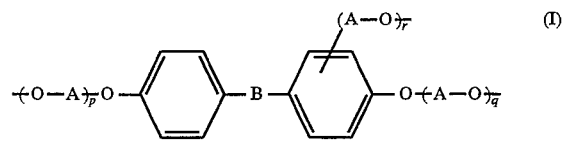

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (—), and p, q and r are each, independently, an integer of 1 to 8; and
      (b) triol units (II) each represented by the following formula (II)

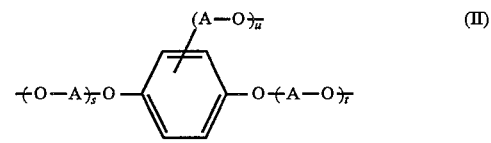

wherein A is a group represented by formula —CH$_2$CH$_2$— or formula —CH(CH$_3$)CH$_2$—, and s, t and u are each, independently, an integer of 1 to 8, in an amount of about 0.01 to 1 mole % based on the sum of the moles of total diol and said triol units.

2. A copolyester comprising:
   (i) diol units consisting essentially of ethylene glycol units and dicarboxylic acid units consisting essentially of terephthalic acid units,
   said copolyester further comprising:
   (ii) at least one group of diol units selected from the group consisting of:

(a) diol units (III) each represented by the following formula (III)

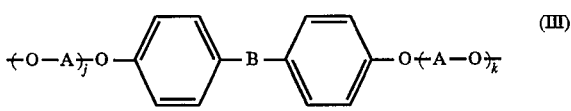

wherein A is a group represented by formula —$CH_2CH_2$— or formula —$CH(CH_3)CH_2$—, B is a divalent hydrocarbon group, a carbonyl group, a sulfonyl group, an oxygen atom or a direct bond (–), and j and k are each, independently, an integer of 1 to 8; and (b) diol units (IV) each represented by the following formula (IV)

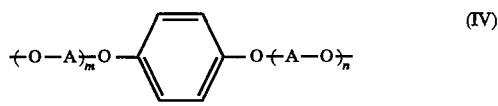

wherein A is a group represented by formula —$CH_2CH_2$— or formula —$CH(CH_3)CH_2$—, and m and n are each, independently, an integer of 1 to 8, and (iii) at least one group of triol units selected from the group consisting of:

(a) triol units (I) each represented by the following formula (I)

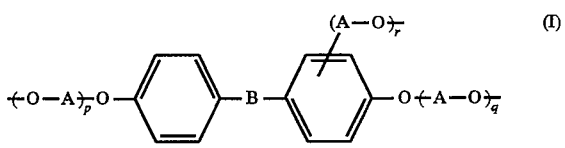

wherein A is a group represented by formula —$CH_2CH_2$— or formula —$CH(CH_3)CH_2$—, B is a divalent hydrocarbon group, a carbonyl group, a sulfonyl group, an oxygen atom or a direct bond (–), and p, q and r are each, independently, an integer of 1 to 8; and (b) triol units (II) each represented by the following formula (II)

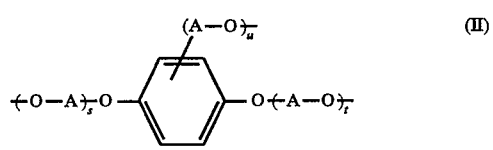

wherein A is a group represented by formula —$CH_2CH_2$— or formula —$CH(CH_3)CH_2$—, and s, t and u are each, independently, an integer of 1 to 8, and (iv) said at least one group of diol units being contained in an amount of about 1 to 15 mole % based on the sum of the moles of total diol units and the moles of the triol units of the above (iii), and (v) said at least one group of triol units being contained in an amount of about 0.01 to 1 mole % based on the sum of the moles of total diol units and the moles of triol units of the above (iii).

3. The copolyester according to claim 1, having an intrinsic viscosity of 0.6 to 1.5 dl/g.

4. The copolyester according to claim 2, having an intrinsic viscosity of 0.6 to 1.5 dl/g.

5. The copolyester according to claim 1, having a melt viscosity ($\eta_1$) at a temperature of 270° C. and at a shear rate of 0.1 rad/sec of $5 \times 10^4$ to $5 \times 10^6$ poises and a melt viscosity ($\eta_2$) at a temperature of 270° C. and at a shear rate of 100 rad/sec of $5 \times 10^3$ to $5 \times 10^5$ poises, said melt viscosity ($\eta_1$) and ($\eta_2$) satisfying the following condition ①

$-0.7 \leq (\frac{1}{3})\log_{10}(\eta_2/\eta_1) \leq -0.2$  ①.

6. The copolyester according to claim 3, having a melt viscosity ($\eta_1$) at a temperature of 270° C. and at a shear rate of 0.1 rad/sec of $5 \times 10^4$ to $5 \times 10^6$ poises and a melt viscosity ($\eta_2$) at a temperature of 270° C. and at a shear rate of 100 rad/sec of $5 \times 10^3$ to $5 \times 10^5$ poises, said melt viscosities ($\eta_1$) and ($\eta_2$) satisfying the following condition ①

$-0.7 \leq (\frac{1}{3})\log_{10}(\eta_2/\eta_1) \leq -0.2$  ①.

7. The copolyester according to claim 2, having a melt viscosity ($\eta_3$) at a temperature of 40° C. above the melting point and at a shear rate of 0.1 rad/sec of $5 \times 10^4$ to $5 \times 10^6$ poises and a melt viscosity ($\eta_4$) at a temperature of 40° C. above the melting point and at a shear rate of 100 rad/sec of $5 \times 10^3$ to $5 \times 10^5$ poises, said melt viscosities ($\eta_3$) and ($\eta_4$) satisfying the following condition ②

$-0.7 \leq (\frac{1}{3})\log_{10}(\eta_4/\eta_3) \leq -0.2$  +e,fra 2+ee .

8. The copolyester according to claim 4, having a melt viscosity ($\eta_3$) at a temperature of 40° C. above the melting point and at a shear rate of 0.1 rad/sec of $5 \times 10^4$ to $5 \times 10^6$ poises and a melt viscosity ($\eta_4$) at a temperature of 40° C. above the melting point and at a shear rate of 100 rad/sec of $5 \times 10^3$ to $5 \times 10^5$ poises, said melt viscosities ($\eta_3$) and ($\eta_4$) satisfying the following condition ②

$-0.7 \leq (\frac{1}{3})\log_{10}(\eta_4/\eta_3) \leq -0.2$  ②.

9. A molded article comprising the copolyester according to claim 1.

10. A molded article comprising the copolyester according to claim 2.

11. The molding article according to claim 9, being an extrusion blow molded article.

12. The molding article according to claim 10, being an extrusion blow molded article.

13. A process for producing molded articles, which comprises subjecting the copolyester according to claim 1 to extrusion blow molding.

14. A process for producing molded articles, which comprises subjecting the copolyester according to claim 2 to extrusion blow molding.

15. A process for producing the copolyester according to claim 1 which comprises subjecting to esterification or transesterification starting material comprising:

(1) a dicarboxylic acid component consisting essentially of terephthalic acid or ester-forming derivatives thereof;

(2) a diol component consisting essentially of ethylene glycol; and (3) a triol component containing at least one triol selected from the group consisting of:

(a) a triol represented by the following formula (V)

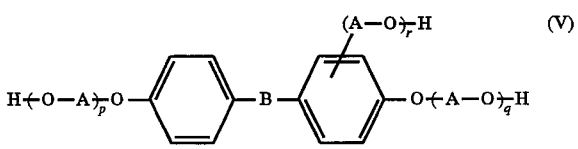

wherein A is a group represented by formula —$CH_2CH_2$— or formula —$CH(CH_3)CH_2$—, B is a

47 divalent hydrocarbon group, a carbonyl group, a sulfonyl group, an oxygen atom or a direct bond (–), and p, q and r are each, independently, an integer of 1 to 8; and (b) a triol represented by the following formula (VI)

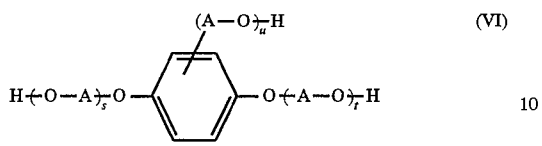 (VI)

wherein A is a group represented by formula —CH$_2$CH$_2$— or formula —CH(CH$_3$)CH$_2$—, and s, t and u are each, independently, an integer of 1 to 8, in an amount of about 0.01 to 1 mole % based on the sum of the moles of total diol and said triol components;

melt polycondensing the obtained reaction product to form a polyester prepolymer; and subjecting the polyester prepolymer to solid phase polymerization.

16. A process for producing the copolyester according to claim 2 which comprises subjecting to esterification or transesterification starting materials comprising:

(1) a dicarboxylic acid component consisting essentially of terephthalic acid or ester-forming derivatives thereof;

(2) a diol component consisting essentially of ethylene glycol and containing at least one diol selected from the group consisting of:

(a) a diol represented by the following formula (VII)

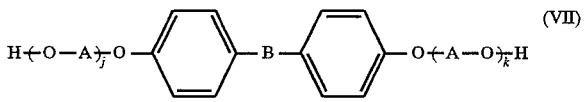 (VII)

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and j and k are each, independently, an integer of 1 to 8; and (b) a diol represented by the following formula (VIII)

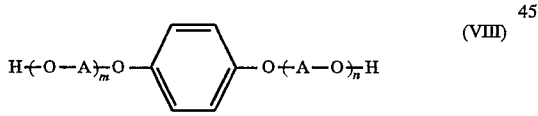 (VIII)

wherein A is a group represented by formula —CH$_2$CH$_2$— or formula —CH(CH$_3$)CH$_2$—, and m and n are each, independently, an integer of 1 to 8, in an amount of about 1 to 15 mole % based on the sum of the moles of total diol and the below-cited triol components; and (3) a triol component containing at least one triol selected from the group consisting of:

(a) a triol represented by the following formula (V)

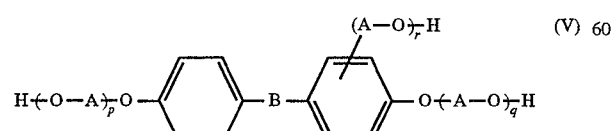 (V)

wherein A is a group represented by formula —CH$_2$CH$_2$— or formula —CH(CH$_3$)CH$_2$—, B is a

48 divalent hydrocarbon group, a carbonyl group, a sulfonyl group, an oxygen atom or a direct bond (–), and p, q and r are each, independently, an integer of 1 to 8; and (b) a triol represented by the following formula (VI)

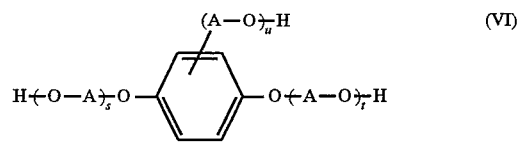 (VI)

wherein A is a group represented by formula —CH$_2$CH$_2$— or formula —CH(CH$_3$)CH$_2$—, and s, t and u are each, independently, an integer of 1 to 8, in an amount of about 0.01 to 1 mole % based on the sum of the moles of total diol and said triol components;

melt polycondensing the obtained reaction product to form a polyester prepolymer; and subjecting the polyester prepolymer to solid phase polymerization.

17. An aromatic triol represented by the following general formula (V)

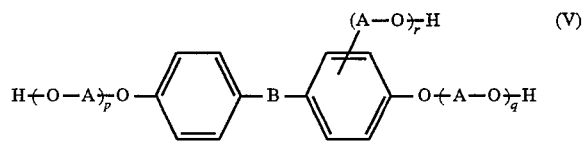 (V)

wherein A is a group represented by formula —CH$_2$CH$_2$— or formula —CH(CH$_3$)CH$_2$—, B is a divalent hydrocarbon group, a carbonyl group, a sulfonyl group, an oxygen atom or a direct bond (–), and p, q and r are each, independently, an integer of 1 to 8.

18. An aromatic triol represented by the following general formula (VI)

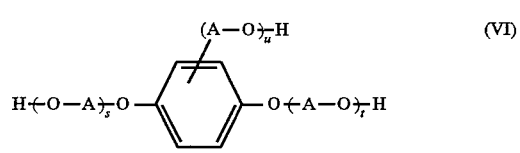 (VI)

wherein A is a group represented by formula —CH$_2$CH$_2$— or formula —CH(CH$_3$)CH$_2$— and s, t and u are each, independently, an integer of 1 to 8.

19. The triol of claim 17 which is 2-[4-(2-hydroxyethoxy)phenyl]-2-[3'-(2-hydroxyethyl)-4'-(2-hydroxyethoxy)phenyl]propane.

20. The triol of claim 18 which is 1,4-bis(2-hydroxyethoxy)-2-(2-hydroxyethyl)benzene.

* * * * *